United States Patent [19]

Behar et al.

[11] Patent Number: 4,853,854

[45] Date of Patent: Aug. 1, 1989

[54] HUMAN BEHAVIOR MODIFICATION WHICH ESTABLISHES AND GENERATES A USER ADAPTIVE WITHDRAWAL SCHEDULE

[75] Inventors: Albert Behar; Orna Behar, both of Reston; Lee W. Frederiksen, McLean, all of Va.; Donald A. Howard-Link, Columbia, Md.; Catherine Timmerman, Washington, D.C.

[73] Assignee: Health Innovations, Inc., Reston, Va.

[21] Appl. No.: 813,401

[22] Filed: Dec. 26, 1985

[51] Int. Cl.⁴ .................. A24F 47/00; G04G 13/02
[52] U.S. Cl. ..................... 364/413.01; 131/270; 364/569; 364/709.02; 364/710.02; 368/10; 368/108
[58] Field of Search ............ 364/413, 415, 569, 709, 364/710; 131/270, 329; 368/10, 107, 108, 109

[56] References Cited

U.S. PATENT DOCUMENTS

| | | | |
|---|---|---|---|
| 2,681,560 | 0/1954 | Shuttleworth | 70/273 |
| 3,424,123 | 1/1969 | Giffard | 131/270 X |
| 3,944,796 | 3/1976 | Fitzpatrick | 364/415 |
| 4,037,719 | 7/1977 | Perlmutter | 206/266 |
| 4,076,118 | 2/1978 | Karlson | 206/268 |
| 4,100,401 | 7/1978 | Tutt et al. | 377/49 |
| 4,144,568 | 3/1979 | Hiller | 364/410 |
| 4,151,831 | 5/1979 | Lester | 128/736 |
| 4,184,202 | 1/1980 | McCrae | 364/413 |
| 4,281,389 | 7/1981 | Smith | 364/569 |
| 4,285,041 | 8/1981 | Smith | 364/415 |
| 4,293,845 | 10/1981 | Villa-Real | 340/309.15 |
| 4,311,448 | 1/1982 | Strauss | 431/14 |
| 4,360,125 | 11/1982 | Martindale et al. | 221/2 |
| 4,366,873 | 1/1983 | Levy et al. | 177/25 |
| 4,428,050 | 1/1984 | Pellegrini et al. | 364/414 |
| 4,459,036 | 7/1984 | Sado et al. | 368/251 |
| 4,493,043 | 1/1985 | Forbath | 364/569 |
| 4,518,267 | 5/1985 | Hepp | 368/107 |
| 4,530,068 | 7/1985 | Nakanishi et al. | 364/900 |
| 4,615,681 | 10/1986 | Schwarz | 131/270 X |
| 4,620,555 | 11/1986 | Schwarz | 131/270 |

OTHER PUBLICATIONS

Fredericksen, L. W. et al., "Development of a Computer Aided Self-Help Smoking Cessation Program", Paper presented at 8th Annual Scientific Sessions of the Society of Behavioral Medicine, Washington, D.C., Mar. 20, 1987.

LifeSign TM advertisement, *Washington Post*, health section, Apr. 28, 1987, 11.

"Computer Programs Range from Calorie Counters to Fitness Coaches", Washington Post Health, Aug. 14, 1985, p. 15.

"Ambulatory Computer-Assisted Therapy for Obesity: A New Frontier for Behavior Therapy" by Burnett et al, J. of Consul. & Clin. Psyc, 1985, vol. 53, No. 5, pp. 698-703.

(List continued on next page.)

*Primary Examiner*—Clark A. Jablon
*Attorney, Agent, or Firm*—Nixon & Vanderhye

[57] ABSTRACT

A human behavior modification method and apparatus aid in withdrawing from a particular habit. A behavioral event such as smoking a cigarette may be associated with the habit numerous times over a period of time. The present method and apparatus aids withdrawal from the habit by providing a structured environment which enables one to reduce the occurrence rate of such behavioral events over a period of time in a way specifically personalized to characteristics of the user's habit. The base line behavioral pattern of a person for a specific habit is measured and used to generate a personalized withdrawal program for the specific habit and user. The user is notified of the withdrawal schedule by means of audio and/or visual stimuli, and the withdrawal program is modified as necessary based on the user's progress during withdrawal. The user interacts with the apparatus by data inputs which are processed by a microprocessor employing a series of computer programs embedded in memory.

31 Claims, 17 Drawing Sheets

OTHER PUBLICATIONS

"Brand Fading: The Effects of Gradual Changes to Low Tar Smoking Rate Carbon Monoxide, and Thiocyanate Levels" by Prue et al, Behavior Therapy, 12, 400–416 (1981).

"Superiority of a Low-Contrast Smoking Cessation Method" by Berecz, Addictive Behavior, vol. 9, pp. 273–278, 1984.

"Prescribed Level of Caloric Restriction in Behavioral Weight Loss Programs" by Wing et al, Addictive Behavior, vol. 6, pp. 139–144, 1981.

"Smoking on Cue: A Behavioral Approach to Smoking Reduction" by Shapiro et al, J. Health & Social Behavior, 12 (Jun.) 1971, pp. 108–113.

"Case Histories and Shorter Communications" by Bernard et al, Behav. Res. & Therapy, 1972, vol. 10, pp. 399–401.

"Clinical Modification of Smoking Behavior" by Fredericksen et al, Modification of Pathological Behavior, Garner Press, Inc., New York, 1979, Chapter 9, pp. 477–556, especially pp. 503–507.

"Smoker Angel"—a one page advertising brochure by CONSO, Bondwell Industrial Ltd. (unknown date).

"Behavioral Engineering: The Reduction of Smoking Behavior by a Conditioning Apparatus and Procedure" by Azrin et al, J. App. Behavior Anal. 1968, I, 193–200.

"A Stimulus Control Approach to the Modification of Smoking Behavior" by Upper et al, Proc., 78th Annual Convention, APA, 1970.

Behavior Therapy (1971) 2, "Smoking Elimination by Gradual Reduction" by Levinson et al, pp. 477–487.

Addictive Behaviors, vol. 2, Pergamon Press 1977. Printed in Great Britain "Temporal Distribution of Smoking" by Frederiksen et al, pp. 187–192.

Addictive Behaviors, vol. 3, Pergamon Press Ltd, 1978, printed in Great Britain, "Measuring Degree of Physical Dependence to Tobacco Smoking with Reference to Individualization of Treatment" by Karl-Olov Fagerstrom, pp. 235–241.

U.S. Patent   Aug. 1, 1989   Sheet 1 of 17   4,853,854
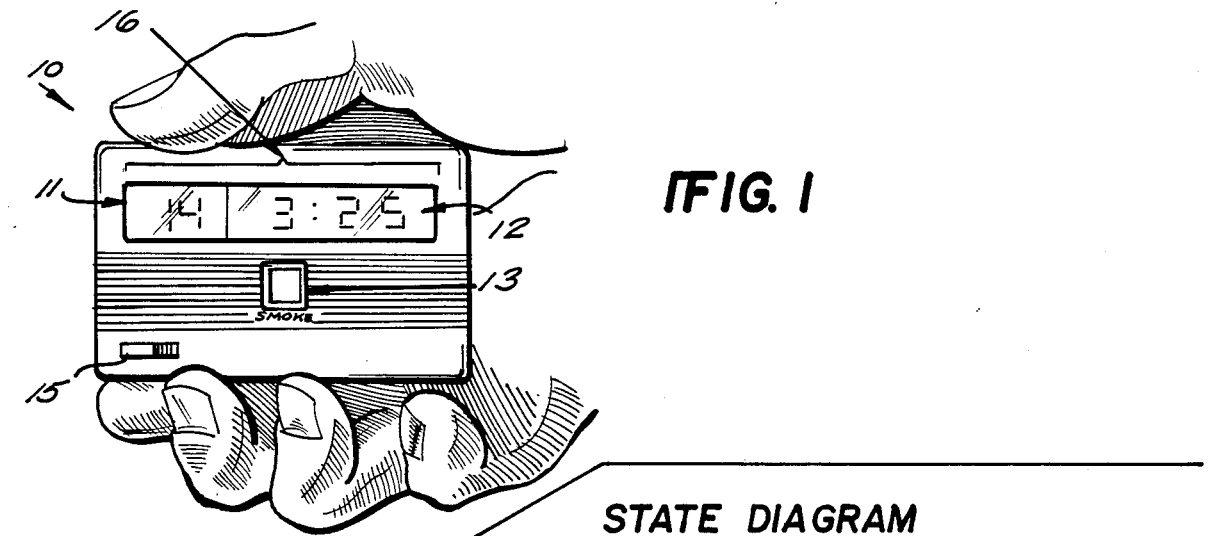
FIG. 1
FIG. 2
STATE DIAGRAM
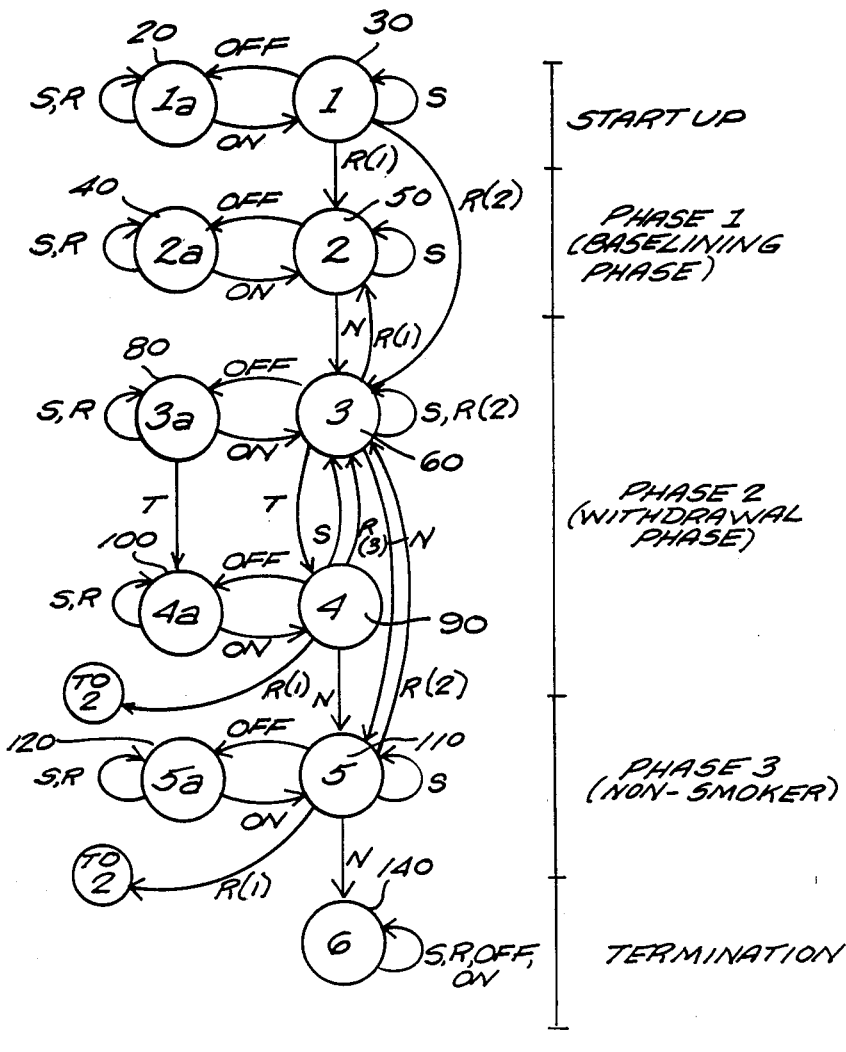

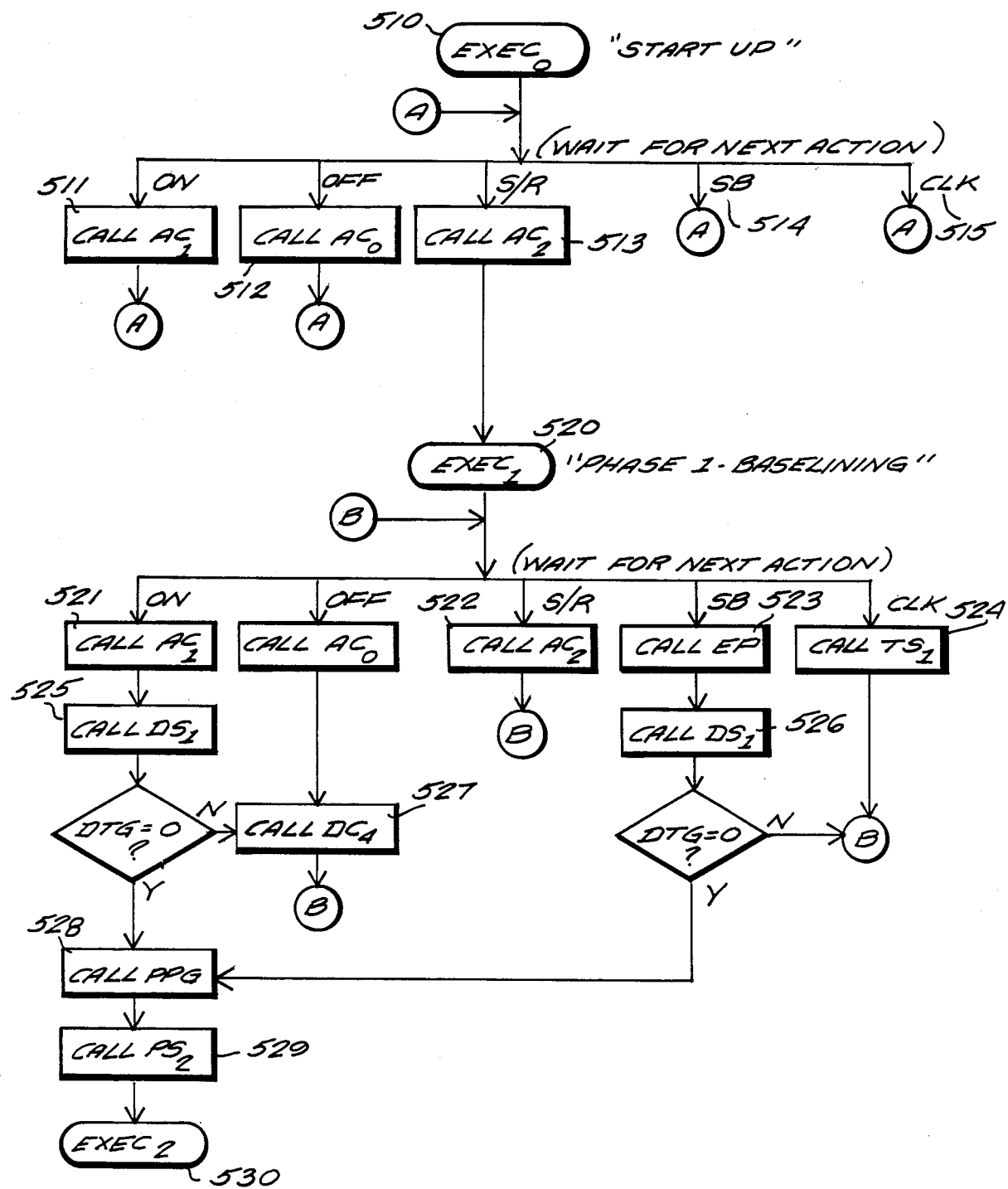
FIG. 5a EXECUTIVE (EXEC)

ACTIVATION CONTROL
(AC)

AUDIO SOURCE
(AS)

FIG. 7a
PHASE SEQUENCER (PS)
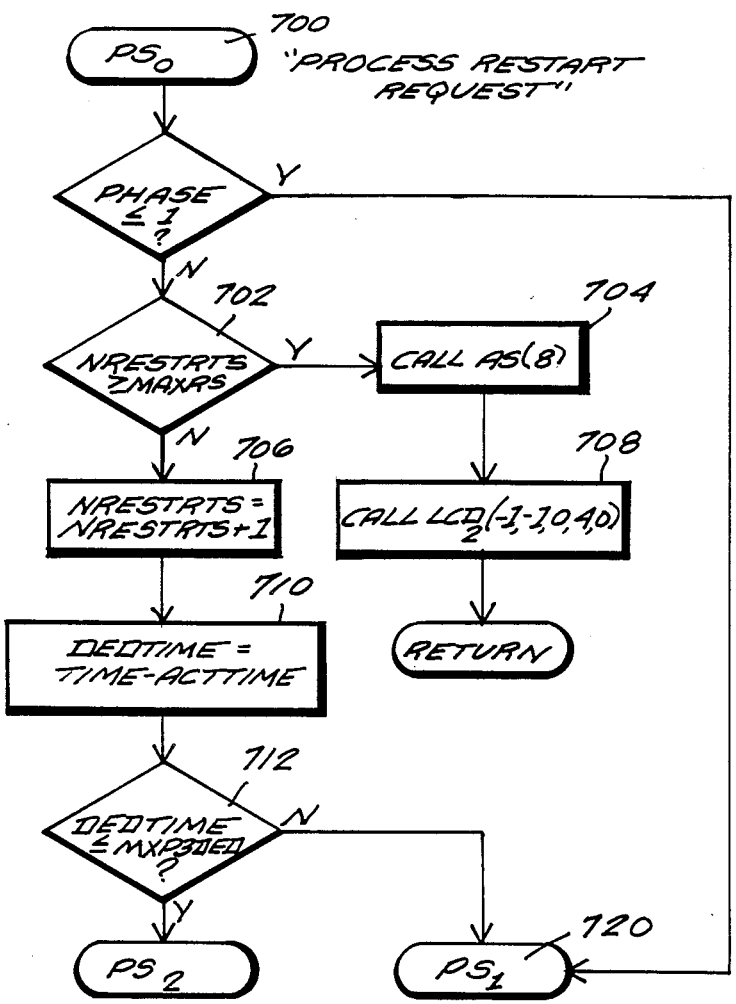
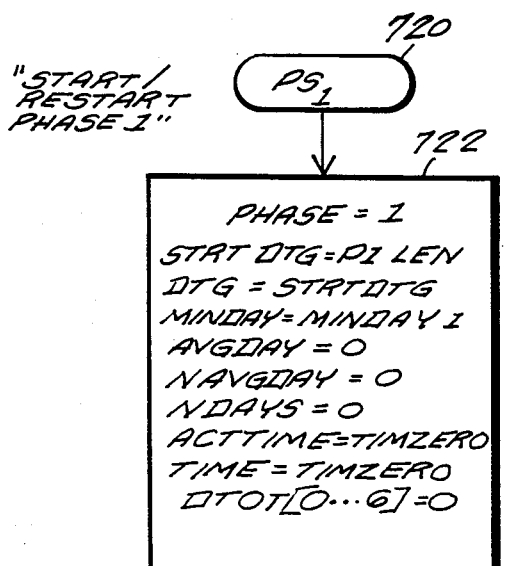
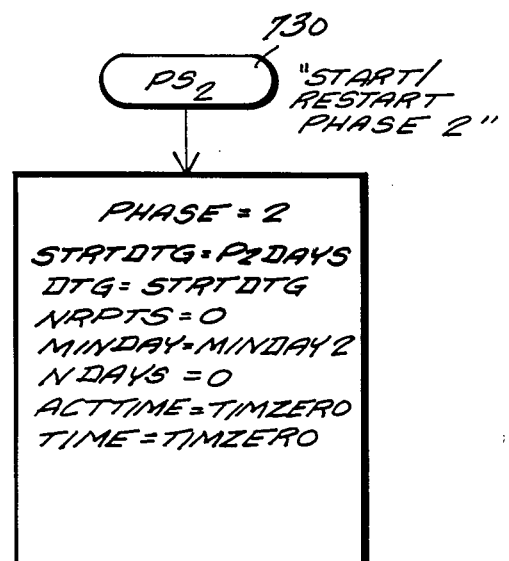
TO FIG. 7b

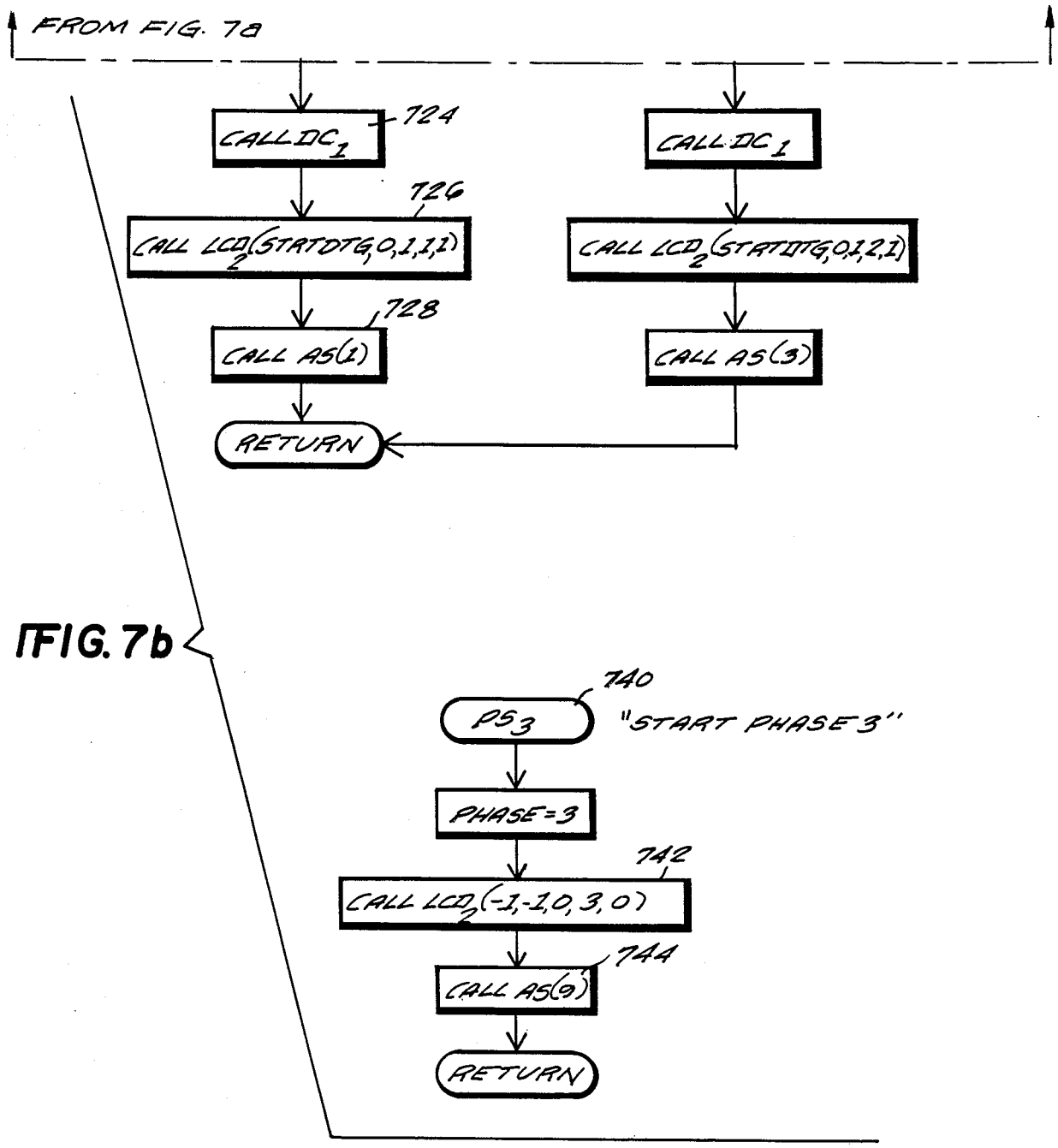
FIG. 7b
FIG. 15
STIMULUS GENERATOR (SG)
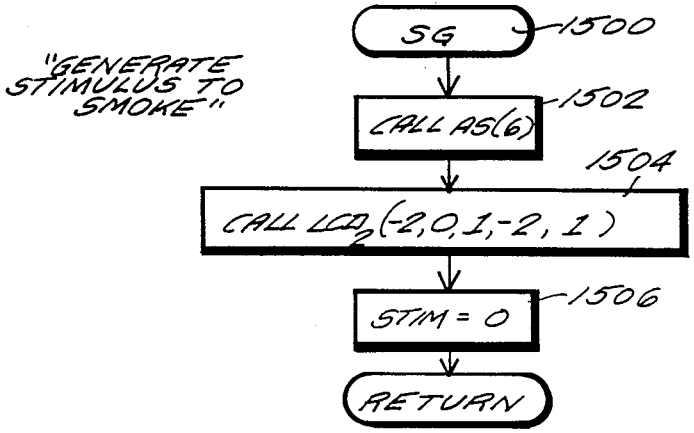

TIME SEQUENCER (TS)

FIG. 10 DAY SEQUENCER (DS)
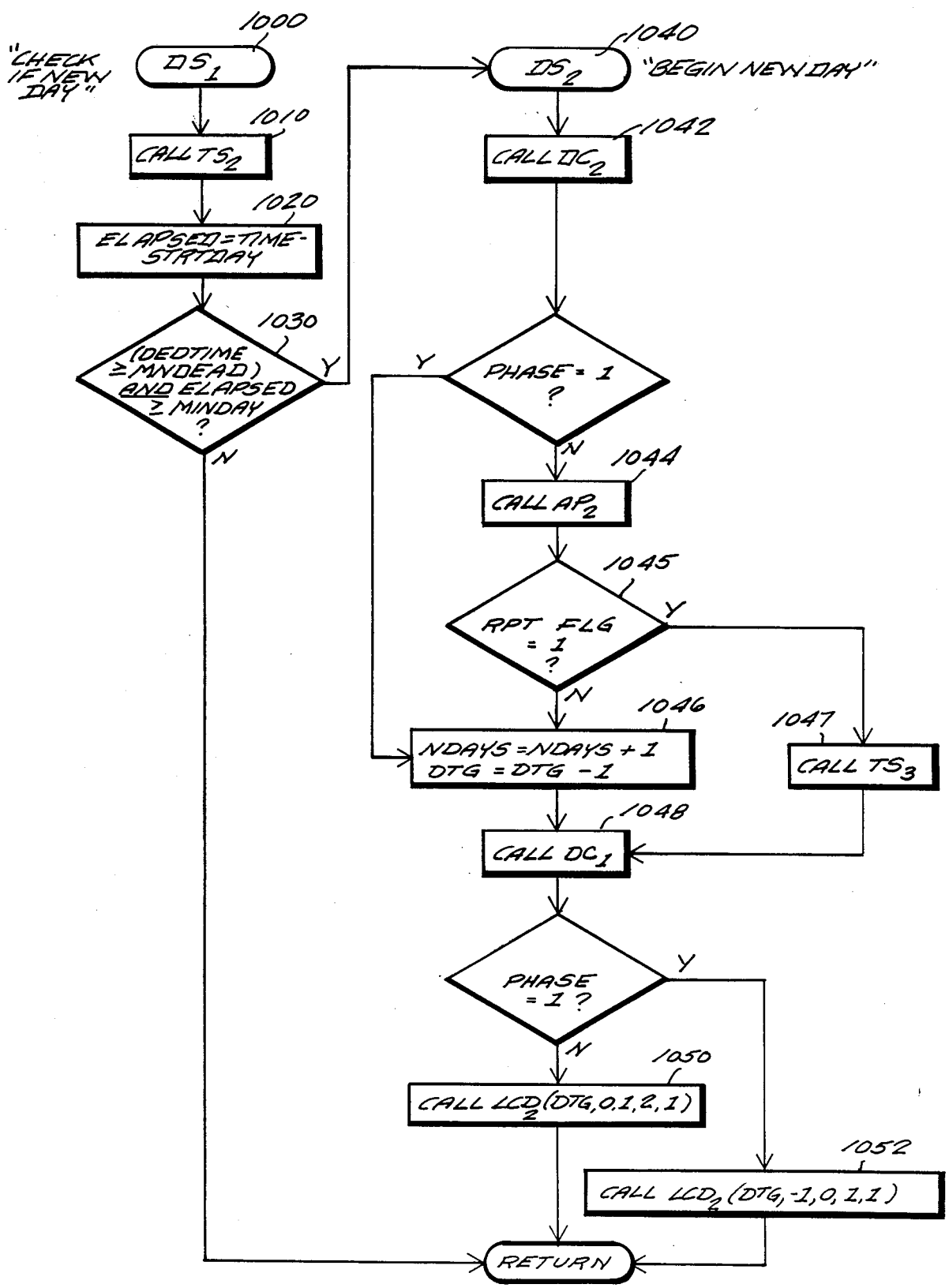

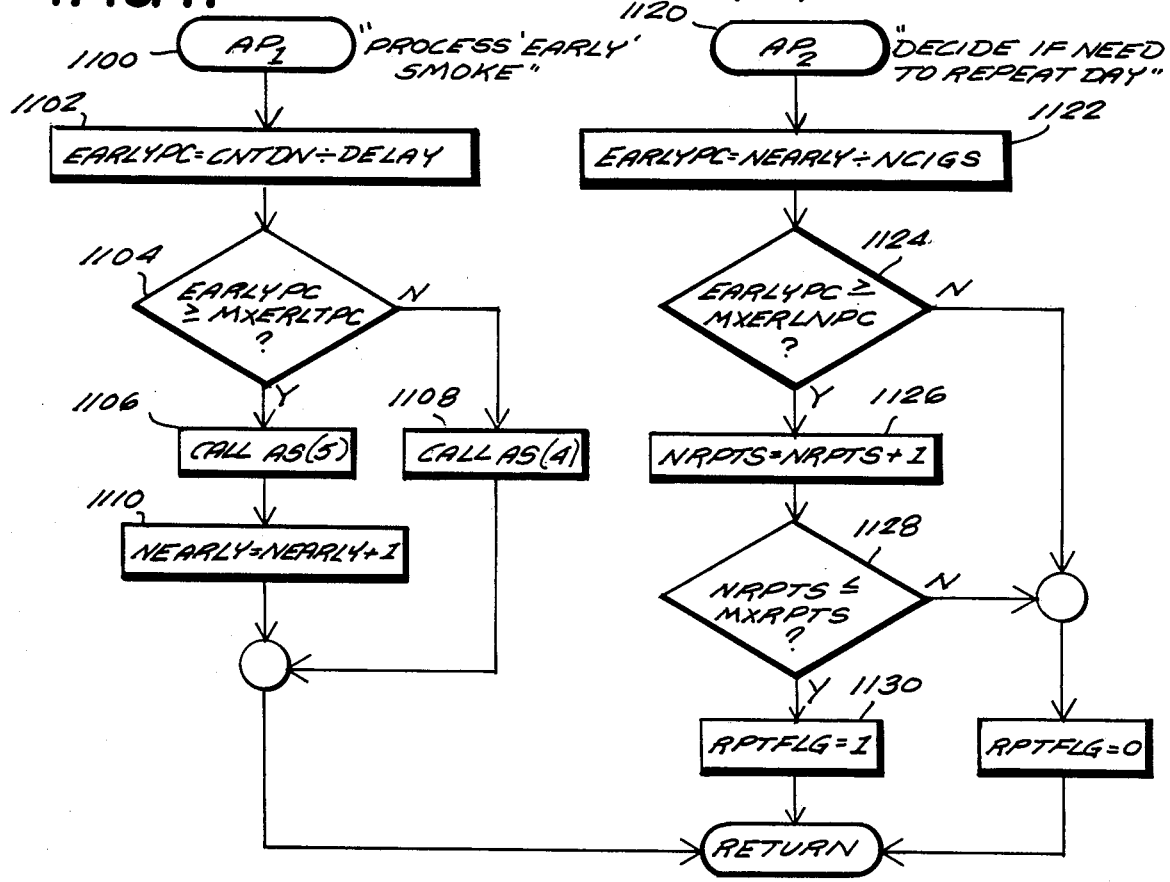
FIG. 11 ADAPTATION PROCESSOR (AP)
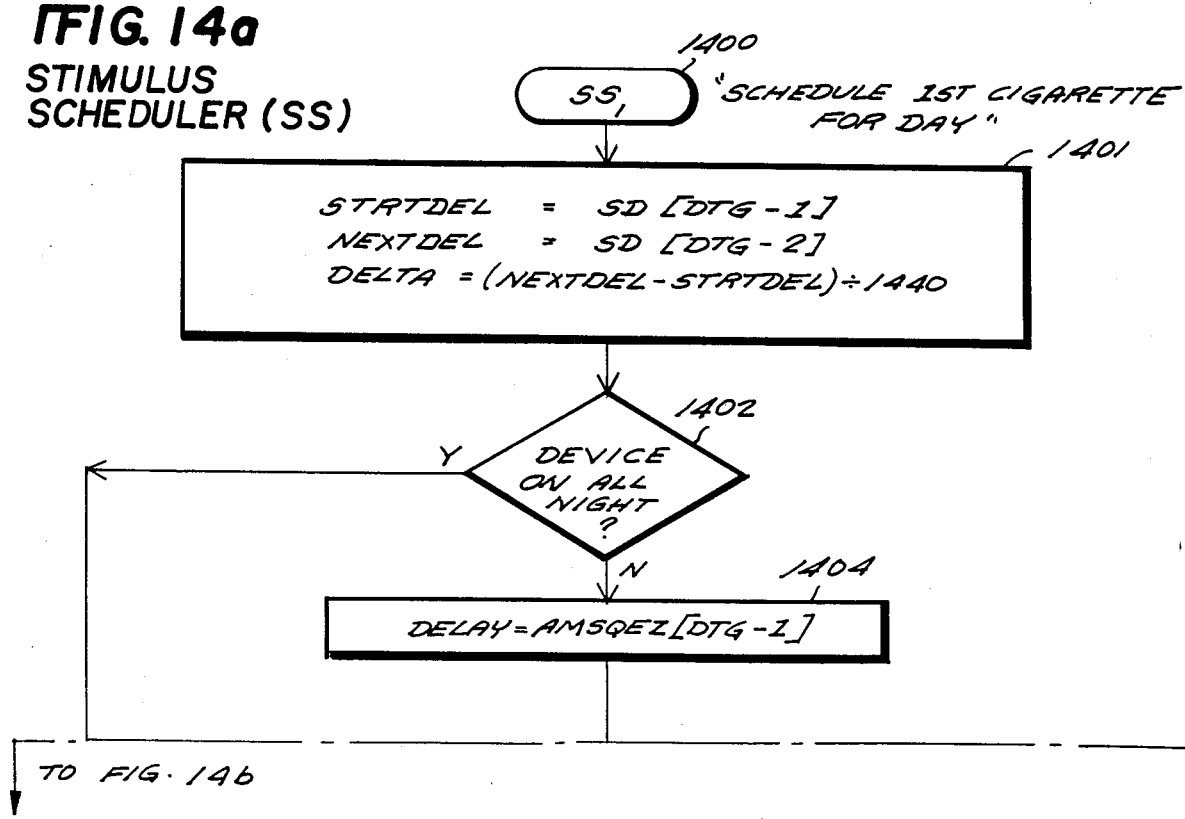
FIG. 14a STIMULUS SCHEDULER (SS)
TO FIG. 14b

FIG. 12 EVENT PROCESSOR
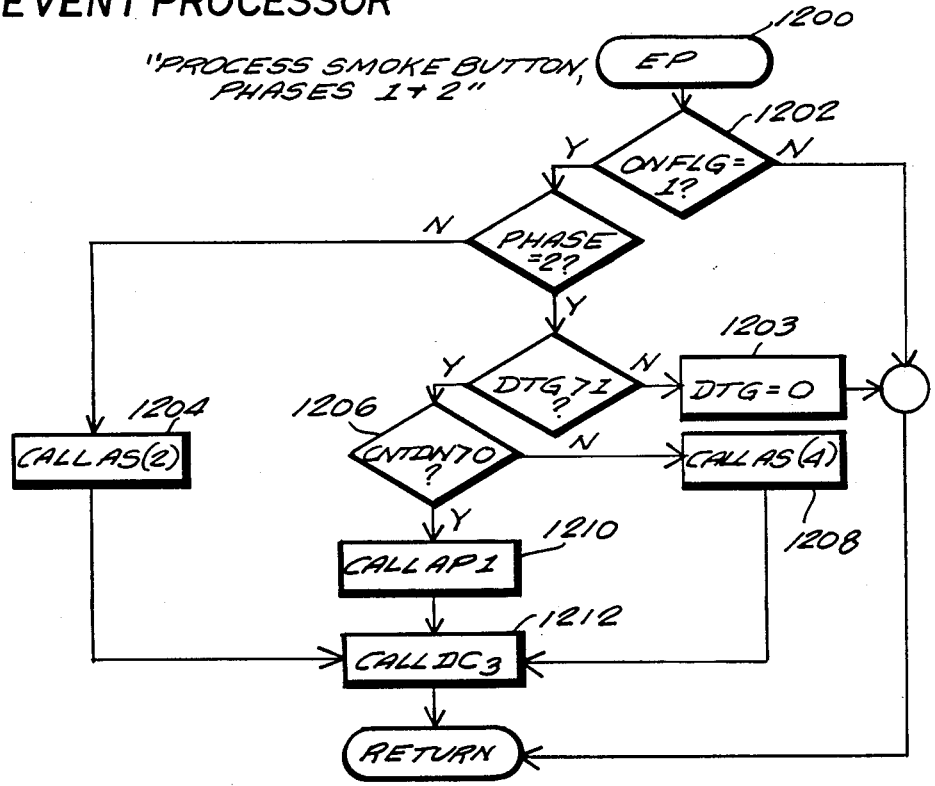
FIG. 13 PERSONALIZED PROGRAM GENERATOR (PPG)
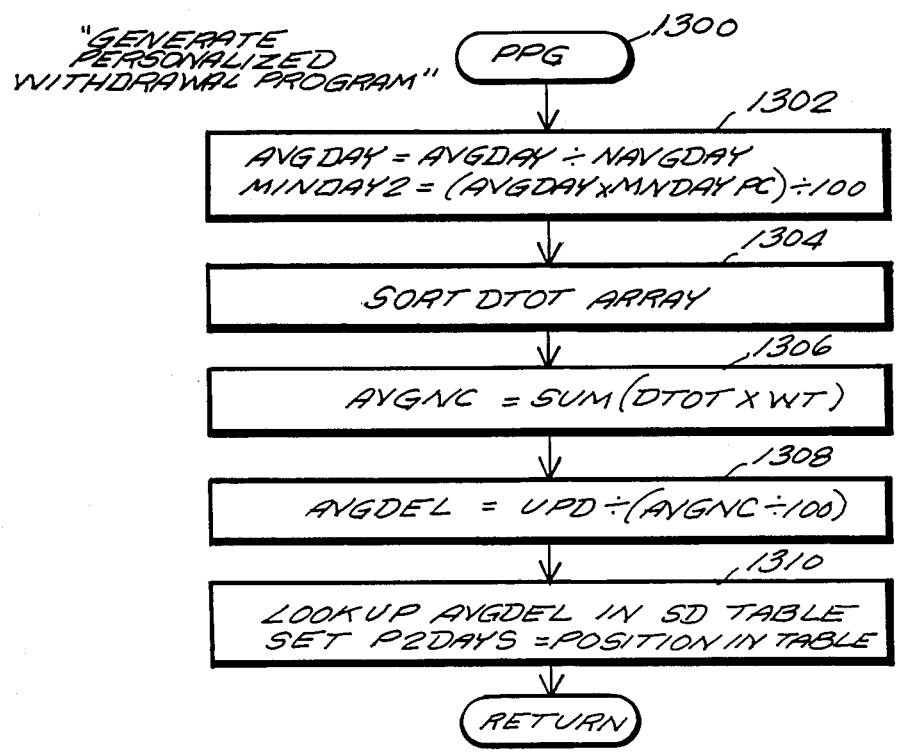

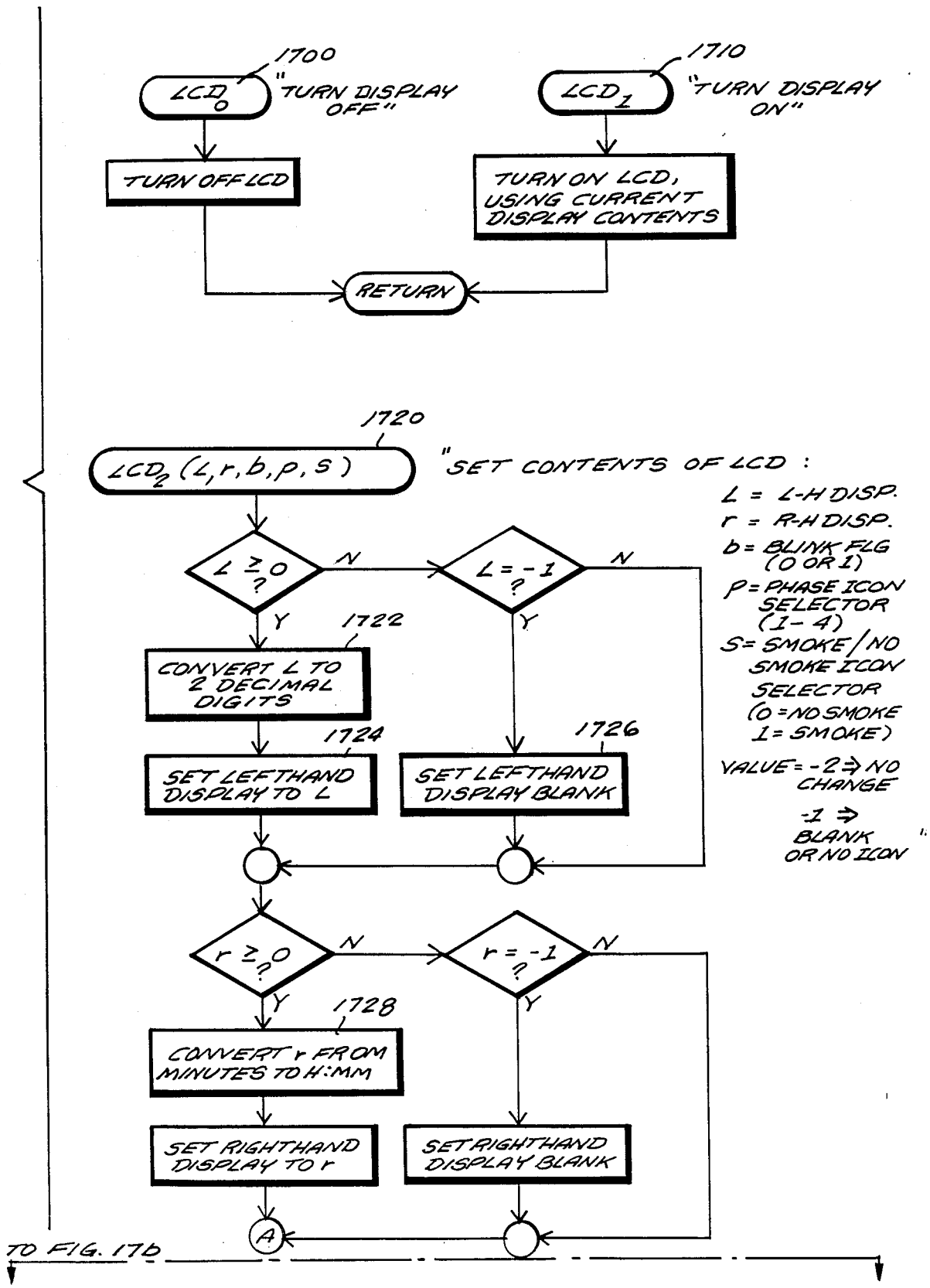
FIG. 17a  LIQUID CRYSTAL DISPLAY (LCD)

HUMAN BEHAVIOR MODIFICATION WHICH ESTABLISHES AND GENERATES A USER ADAPTIVE WITHDRAWAL SCHEDULE

BACKGROUND OF THE INVENTION

This invention is generally directed to an apparatus and method for behavioral modification. The presently preferred exemplary embodiment employs an adaptive withdrawal especially suited for modifying human behavior to withdraw from the habit of smoking. The exemplary apparatus and method is also can be suited for modification of other habit behaviorisms as will be appreciated.

There are many compulsive habits such as smoking where a user performs an event associated with the habit many times during the course of a day. Many of these habits have chemical addiction associated with them. Any withdrawal from such habits may be made easier if the addictive agent of the habit can be reduced, over a period of time by a method specifically tailored to the characteristics of the addiction of a particular person.

There have been many past attempts to achieve suitable methods and/or apparatus for assistance in achieving cessation (or at least a reduction) of smoking activites. Some (non-exhaustive) examples are provided in the following prior published documents:

"Smoker Angel"—a one page advertising brochure by CONSO, Bondwell Industrial Ltd. (unknown date).

"Behavioral Engineering: The Reduction Of Smoking Behavior By A Conditioning Apparatus And Procedure" by Azrin et al, *J. App. Behavior Anal.*, 1968, I, 193–200.

"A Stimulus Control Approach To The Modification Of Smoking Behavior" by Upper et al, *Proc., 78th Annual Convention, APA*, 1970.

"Smoking Elimination By Gradual Reduction" by Levinson et al, *Behavior Therapy* (1971), 2, 477–487.

"Smoking On Cue: A Behavioral Approach To Smoking Reduction" by Shapiro et al, *J. Health & Social Behavior*, 12 (June), 1971, pp. 108–113.

"Case Histories and Shorter Communications" by Bernard et al, *Behav. Res. & Therapy*, 1972, Vol. 10, pp. 399–401.

"Clinical Modification of Smoking Behavior" by Fredericksen et al, *Modification of Pathological Behavior*, Garner Press, Inc., New York, 1979, Chapter 9, pp. 477–556, especially pp. 503–507.

"Brand Fading: The Effects of Gradual Changes to Low Tar Smoking Rate, Carbon Monoxide, andn Thiocyanate Levels" by Prue et al, *Behavior Therapy*, 12, 400–416 (1981).

"Superiority Of A Low-Contrast Smoking Cessation Method" by Berecz, *Addictive Behavior*, Vol. 9, pp. 273–278, 1984.

U.S. Pat. No. 2,681,560—Shuttleworth (1954).
U.S. Pat. No. 3,424,123—Giffard (1969).
U.S. Pat. No. 4,037,719—Perlmutter (1977).
U.S. Pat. No. 4,076,118—Karlson (1978).

The Smoker Angel brochure describes what appears to be a handheld computer device which provides a display of the number of cigarettes smoked, an average of the number smoked over some interval, the just-passed inter-cigarette time interval, the amount of tar consumed, a no-smoking icon if the number of cigarettes smoked exceeds some threshold—as well as typical time-clock functions. Attempts to contact the manufacturer/ distributor have failed and the only known accessible specimen of this device is inoperative.

The above-referenced published papers generally recognize the use of "pocket-timers" and the like to cue a user as to the next permitted smoke during a withdrawal phase. Some also recognize the possible value of establishing a personalized withdrawal schedule based on observations during a first baseline phase. However, none appear to contemplate an automatic programmed user-activated and user-implemented base-line phase followed by automatic generation and implementation of an (adaptive) withdrawal phase. Special attention is drawn to coinventor Frederiksen's 1979 publication, and especially to pages 503–507 thereof for a more detailed description and evaluation of some prior approaches.

The prior art patents referenced above merely involve time-interval locks or the like on cigarette containers.

With respect to prior personalized (e.g. hand-held) programmed devices for assisting/ monitoring/recording/controlling various types of human user behavior, attention is drawn to the following representative prior art:

U.S. Pat. No. 4,100,401—Tutt et al (1978)
U.S. Pat. No. 4,144,568—Hiller (1979)
U.S. Pat. No. 4,151,831—Lester (1979)
U.S. Pat. No. 4,184,202—McCrae (1980)
U.S. Pat. No. 4,281,389—Smith (1981)
U.S. Pat. No. 4,285,041—Smith (1981)
U.S. Pat. No. 4,360,125—Martindale et al (1982)
U.S. Pat. No. 4,428,050—Pellegrini et al (1984)
U.S. Pat. No. 4,459,036—Sado et al (1984)
U.S. Pat. No. 4,493,043—Forbath (1985)
U.S. Pat. No. 4,530,068—Nakanishi et al (1985)

"Prescribed Level Of Caloric Restriction In Behavioral Weight Loss Programs" by Wing et al, *Addictive Behaviors*, Vol. 6, pp. 139–144, 1981.

"Computer Programs Range From Calorie Counters To Fitness Coaches", *Washington Post Health*, Aug. 14, 1985, p. 15.

"Ambulatory Computer-Assisted Therapy For Obesity: A New Frontier For Behavior Therapy" by Burnett et al, *J. of Consul. & Clin. Psyc.*, 1985, Vol. 53, No. 5, pp. 698–703.

The Tutt et al device is interesting in that it permits a user to input data respresenting caloric intake as well as estimated caloric expenditure rates. The device then displays the instantaneous net balance of unconsumed calories. The stated object is to provide the user with such accounting data so that the user is better enabled to modify future caloric intake and/or activity so as to achieve desired dieting results. However, Tutt et al do not appear to define any base line data gathering period—nor do Tutt et al generate any personalized program for behavior modification, let alone any personalized programmed schedule of future occurrence event times.

Hiller et al, Lester and McCrae all appear to merely record various pesonalized data and to provide processed related output data to the user. While the output data may be of interest to the user and might conceivably affect the user's future activities, none of these devices actually stimulate human behavior modification in any meaningful sense. Certainly none of them attempt to change a predetermined pattern of habitual human behavior— nor do any of them monitor a time-sequence of events naturally occurring as a part of habitual behavior and then to responsively generate a personalized program for modification of such habitual behavior.

The two Smith patents are perhaps of more interest in that they describe a device which is programmed to provide personalized metronome-like audible signals designed to pace every other stride of a long distance runner. Although the necessary data may be manually input prior to the run, it is also possible for the runner to manipulate accessible controls and modify the programming so as to conform with his actual stride frequency during a given run. Thereafter, the device is apparently capable of subsequently providing a modified programmed stride rate (e.g. during a later "split" portion of the race) so as to signal the stride rate required to make up for lost time.

Martindale et al show a medicine dispenser which signals the user each time a medication event is supposed to occur—and also records the time at which each medicine access by the user actually occurs. However, the device appears designed only to provide a doctor with such a factual record—and no attempt is made to create any modified program schedule or the like for the future.

Pellegrino accepts personalized input data relating to skin tanning parameters and then provides the user with a program which should be followed so as to achieve a desired degree of tanning. There does not appear to be any initial "baseline" learning phase or the like—nor is this device actually directed toward modification of habitual human behavior associated with a time-sequence of events.

The remaining Sado et al, Forbath and Nakaniski et al references are merely representative of personalized scheduling/timing/memory devices and are in no way suggestive of human behavior modification apparatus/-method.

The additional publications are also generally exemplary of prior attempts to use small personal computers to monitor and/or modify certain human behavior. Burnett is especially interesting in its suggestion of using a small interactive micro-computer carried by a user and used to provide self-monitoring/feedback functions in an attempt to help the user lose weight.

Although all these prior approaches are of general interest, none is yet believed to provide an optimum solution to the problem of modifying habitual human behavior associated with a time sequence of events (e.g. the smoking of cigarettes).

BRIEF SUMMARY OF THE INVENTION

An exemplary embodiment of the present invention provides an apparatus and method for measuring parameters of current user behavior for a specific addictive habit. The resulting behavioral pattern is used to generate a personalized withdrawal program for the specific addictive habit of a specific user and the user is notified of the withdrawal schedule by means of audible and visible stimuli. The withdrawal program may be automatically modified as necessary based on the user's progress during withdrawal.

The exemplary embodiment facilitates withdrawal from the habit of smoking, and is based upon certain psychological foundations such as (1) stimulus control, (2) placebo value and (3) decision minimization. With regard to stimulus control, people that smoke often light a cigarette only half-consciously in response to cues and activites which they repeatedly have been conditioned to associate with smoking. For example, when smoking is frequently paired with enjoyable activities, the smoker will likely feel an urge to smoke each time he engages in such an activity. Breaking the psychological link between smoking and these activities can greatly facilitate successful smoking cessation. The present invention helps solve this problem of stimulus control by placing the smoker on a regime based on elapsed time, rather than the activities of the person's day.

There is a placebo value to use of this invention in that the apparatus contains a microprocessor which constructs and controls a behavior modification plan and thus may evoke a positive expectancy of success. People have been conditioned to rely upon science and computers. Therefore many smokers are apt to have high expectations of success when aided by a small computer which develops a personalized program for smoking cessation.

Decision minimization is another important factor in successful cessation. A significant difficulty which occurs when a smoker tries to quit by gradual withdrawal, is the discomfort of repeated decisions as to whether the smoker should smoke immediately or wait a little longer until smoking the next cigarette. This continuous tension between wanting to smoke and the desire to maintain the withdrawal can be exhausting and may lead to abandonment of the smoker's effort to withdraw. The present invention solves this problem by eliminating the burden of having to decide when it is appropriate to smoke the next cigarette. The device signals the user as to when it is appropriate to smoke the next cigarette.

The invention may also be used with associated techniques for aiding the individual to withdraw from the addictive habit. Such techniques include, by way of non-limiting example: use of certain dietary strictures to minimize weight gain and to eliminate substances that increase the craving for cigarettes; a light exercise program to minimize weight gain and also to reduce tension; a strategy for gaining the necessary social support for breaking the smoking habit; and a self-managed reward system for successfully quiting.

The presently preferred exemplary embodiment includes a small pocket-sized device that is controlled by a microprocessor, programmed in read-only memory with the specific control program for a particular addictive habit. The device is powered by a battery that has a sufficient life to run the device continually during a complete behavioral modification cycle. The microprocessor and associated circuitry for interfacing and programming are all contained within the device.

In operation, the user activates the device by a switch or other actuator located on the device in such a way that a conscious effort is required for activation. This initial activation of the device causes the device to commence a base line establishment phase of the behavioral modification process. Each time the user commits a habit event, he informs the device by one or more activations using a mechanism such as recessed switch button or the like. The device records the event at the time of its occurrence (as signified by switch activation) for future processing.

The device remains in the baselining phase for a period of time predemined by the computer program for a specific behavior modification program. When the baselining phase is over, the device notifies the user via visual and/or audio stimuli, and proceeds to a withdrawal phase.

When the personalized withdrawal phase begins, the device prompts the user by providing visual and/or audio stimuli as to when the user may indulge in the addicting habit. The device also provides information to the user regarding the necessary dosage, portion or other parameters appropriate for cessation of a specific habit. In the case of smoking withdrawal, the user is prompted to smoke one cigarette upon being prompted by the stimuli. A visual display also informs the user as to when permission to indulge in another addictive event will next be signaled. The user notifies the device that the prescribed event has been committed by activating a mechanism (e.g., a switch) on the apparatus. If the user cannot wait until the prescribed time, the user also can indicate an early event via the device. The unit then takes account of this "early" event and adapts the withdrawal plan by rescheduling allowed smoking events based on the actual withdrawal performance of the user. Besides displaying the time until the next allowed addictive event, the exemplary device also displays the time remaining until the end of the entire withdrawal phase.

BRIEF DESCRIPTION OF THE DRAWINGS

Further objects and advantages of the present invention will be better understood by carefully reading the following detailed description of the presently preferred exemplary embodiment of this invention in conjunction with the accompanying drawings, of which:

FIG. 1 is a front external view of the exemplary embodiment;

FIG. 2 is a state diagram for the exemplary embodiment;

FIGS. 5a, 5b, 6, 7a, 7b, 8–13, 14a, 14b, 15, 16, 17a and 17b are flow diagrams of relevant portions of an exemplary computer controlling program for use in realizing the system functions of FIGS. 2–3.

DETAILED DESCRIPTION OF THE EXEMPLARY EMBODIMENT

Figure 3:
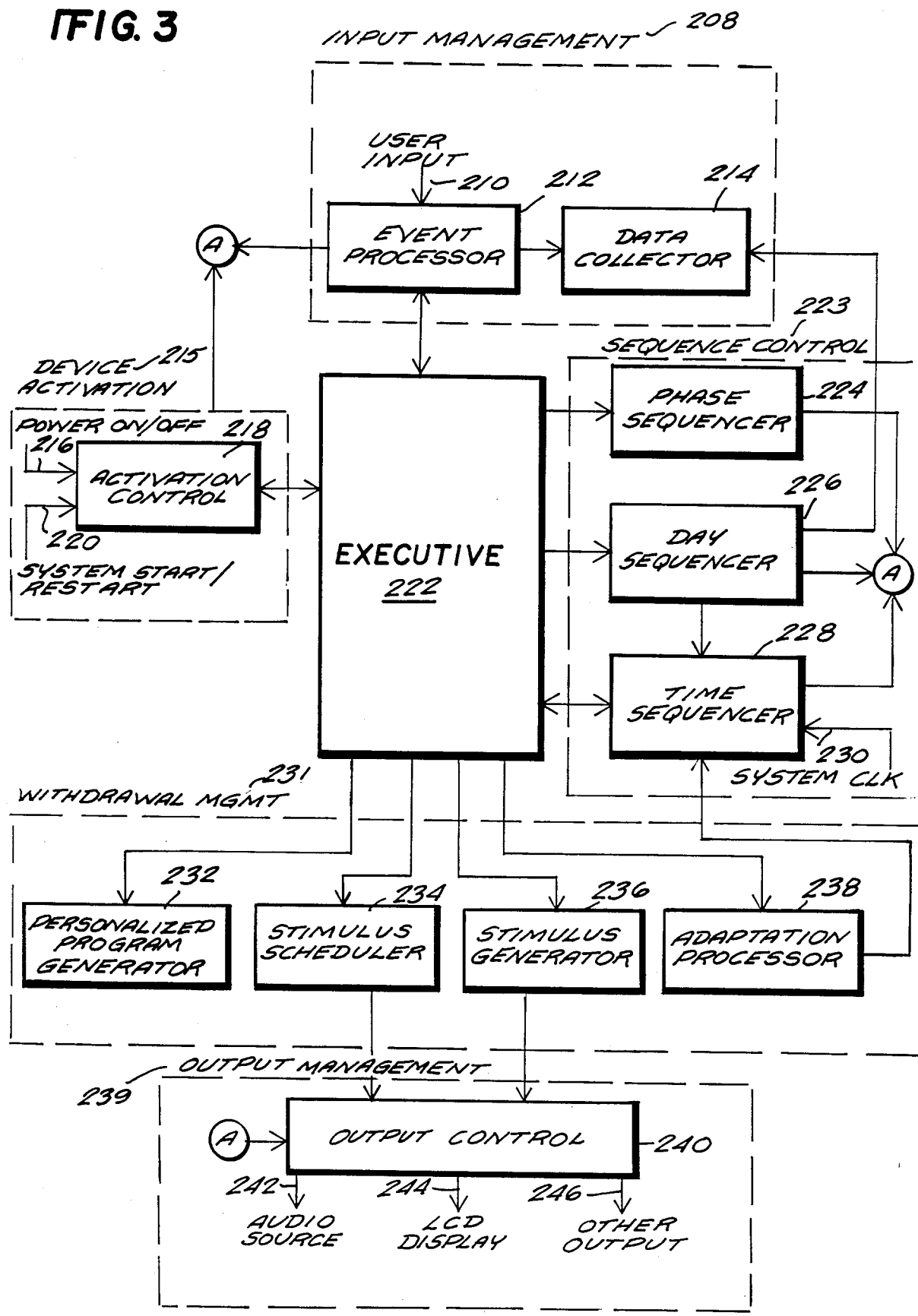
FIG. 3 is a functional block diagram of "software" implemented exemplary embodiment functions showing major functional system components.

As shown in FIG. 1, the preferred exemplary embodiment (used for smoking withdrawal), is a generally rectangular device 10 which can typically be held in a person's hand with the on/off switch 15 of the device located in the lower left corner. The on/off switch 15 activates the operating state of the device and is not to be confused with a start/restart switch located on the back of the device (not shown). The liquid crystal display (LCD) 16 shows the number of days remaining until the end of a current behavior modification plan phase at the left side 11 of the LCD. The right side 12 of the LCD shows the time remaining until the next prescribed smoking event during the withdrawal phase. A "smoke" button switch 13 is located at the center of the device and the user activates it to record each committed smoking event.

The incorporation of such devices per se into such a small package may use conventional apparatus and construction techniques.

FIG. 2 shows a state diagram illustrating the basic operation of the device. At the initiation of start-up, the user normally receives the device in an "off" condition as depicted in state 1a-20. At this point the LCD 16 is blank. Whenever the device is off, the smoke button 13 and restart button are ignored. Thus, state 1a-20, state 2a-40, state 3a-80, state 4a-100 and state 5a-120 are states that may occur when the device is off. When the device is turned "on", for all states other than state 6-140, an audible acknowledgement is given via the audio source. With the device in state 1-30 the user presses the restart button to begin operation of the baselining phase. From start-up the transition is from state 1-30 to state 2-50. This transition is announced via a short melody by the audio source.

The baselining phase begins in state 2-50. The device is on with the LCD 16 showing the number of days remaining or "days to go" (DTG) in the baselining phase on the left hand portion 11 of the LCD and the right hand side 12 of the LCD showing blank. The DTG value is defined in the software and is normally 7 days.

The user now begins recording smoking activity by pressing button 13 each time the user smokes. Each activation of the smoke button 13 is acknowledged by a short "beep" from the audio source. The total number of smoking events for each day is recorded. At the end of the day, the user turns the device off causing a change in state, to state 2a-40. The user turns the device on again the next morning and thus the device returns to state 2-50. This normal operation results in software determination that a new day has begun for the user and the DTG display is decreased by one.

If the user operates the device in an abnormal manner (e.g., leaves the device on all night or turns the device off during the day) the software nevertheless makes an effort to correctly recognize the start of a new day. This is checked each time the user presses either the "on" button 15 or the smoke button 13. In addition to the total number of smoking events for the day, the average length of the user's "waking" day is also computed. Unusually short or long days are effectively ignored so as not to distort calculated averages. A very long period of inactivity (e.g., several days) is also effectively ignored.

Thus a seven-day baselining phase may actually last more than seven days real time. The baselining phase has a duration of time as long as is required to collect sufficient data.

At the end of the baselining phase, the next new day results in an automatic transition to a withdrawal phase from state 2-50 to state 3-60. As part of this transition, data collected during the baselining phase is analyzed and key parameter values controlling the withdrawal phase are determined (calculated or referenced in a table). The start of the withdrawal phase is announced by a short melody from the audio source. If at any point during the baselining phase, the user needs to restart from the beginning, the user presses the restart button with the device on. The start of the baselining phase is signaled by a melody being played again by the audio source, the DTG value is reset to its starting value (usually 7), and the LCD 16 is updated accordingly.

The withdrawal phase begins at state 3-60. The device is on with the LCD 16 showing the DTG number of days in the withdrawal phase on the left side 11 and the time until the next prescribed smoking event at the end of the baselining phase based on the user's own smoking rate and possibly other user parameters. Hence, the user hears a melody announcing the start of the withdrawal phase, observes how many days it will take to quit smoking, and the time remaining until he/she can next commit a smoking event.

As time passes, the right side 12 of the LCD is updated each minute to show the time-to-smoke value counting down. If the device is turned off by the on/off switch 15, then LCD 16 becomes blank. The countdown of time, however, continues and will display such at the right side 12 of the LD when the on/off switch 15 is again turned to the on position.

When the countdown reaches zero time remaining until the next allowed smoking event, state 4-90 is entered (state 4a-100 is entered if the device is off). If the device is on, a short signal is sounded by the audio speaker 14 to inform the user that the user may now commit a smoking event. A visual indication that the user may now smoke is also displayed on the right side 12 of the LCD remains until the user next presses the smoke button 13.

During typical use, the device counts down to zero time remaining until the next allowed smoking event, sounds a signal informing the user that it is time to smoke, and if the user smokes, the smoke button 13 is to be activated. The actual smoking event is recorded by the device and a new time-to-smoke value is determined and displayed, returning the device back to state 3-60. The new time-to-smoke value is based on the current DTG value and on the elapsed time since the current day began. Time-to-smoke values (i.e., the elapsed time between permitted smokes) will increase from day-to-day, based on a prescribed withdrawal curve and will increase linearly with time over any given day.

In some cases the user will smoke before the countdown reaches zero while still in state 3-60. In this case, both the smoking event and an indication as to how much earlier the smoking event occurred than was planned, are recorded for use at the start of the next day. A new time-to-smoke value is determined, and the device remains in state 3-60, counting down to the next smoke signal.

An analysis of early smoking events is used to determine (at the start of each new day) whether to go on to the next day with a commensurate decrease in DTG value, or repeat the day just completed. This feature enables the device to adapt a behavioral modification plan to the user who has difficulty in complying with the scheduled smoke withdrawal regime, by providing the user a second chance to accomplish the prescribed schedule on a given day. The number of repeated days allowed and the overall extent of adaption is controlled by internal parameters.

A curfew period is determined for each day of the withdrawal phase. Once in this curfew period, no new countdowns will be initiated, although a currently running countdown will be completed. Once the user presses the smoke button 13 for the last signaled cigarette for that particular day, the right portion 12 of the LCD is changed to display a "don't smoke" indicator of some type (e.g., an icon). The user's last smoke can fall either in or out of the curfew period. If the next smoking event is scheduled to fall only *slightly* (as defined by a parameter value) inside the curfew, it will be scheduled normally and will be the last one scheduled for that particular day. If, however, the next smoking event is scheduled to fall *substantially* inside the curfew period (as also defined by a parameter value), it is not scheduled, and the smoking event just completed becomes the last scheduled smoking event for that particular day.

As in the baselining phase, the user is instructed (by an accompanying manual) to turn the device off each night and on again each morning. A determination is made by the software of when each new day begins. This determnation is based on two factors: (1) the fact that the device was unused for an unreasonably long period and (2) the day is long enough to be a complete day. Special handling is required for the user who leaves the device "on" all night. When such a user begins the next day, the right side 12 of the LCD will show either the "o.k. to smoke" indicator or the "don't smoke" indicator, depending on how soon that day the user looks at the device. The "don't smoke" indicator is displayed following the previous day's last smoke, and remains in effect until the time at which the user would be expected to have a first smoke for the new day had the user operated the device normally. This point in time is determined based on the user's average sleep and wake times and on the current DTG value indicated at the left side 11 of the LCD. When this time is reached, the normal smoke signal is also given (assuming the device is on), via the audio source.

The withdrawal phase operation continues for the planned number of days (not counting repeats). Once the last smoking event on the last day is recorded, a transition to the non-smoker phase is automatically performed and is announced by a substantial melody via the audio source. Note that at any time during the withdrawal phase, however, the user may restart the cessation program by pressing the restart button. A determnation is made whether to restart at the baselining phase or at the withdrawal phase. When the restart is performed, the corresponding announcement melody for that phase is sounded via the audio source. Note, however that only a limited number of restarts from the withdrawal phase are allowed in the exemplary embodiment (controlled via an internal parameter). Additional attempts to restart will be ignored. Once the last permitted pass through the withdrawal phase is completed, an automatic transition will be made to state 6-140 where the device becomes inoperative for the user.

Once the withdrawal phase has been completed, the user enters the non-smoker phase. The user will keep the device in case of relapse. The non-smoker phase begins at state 5-110 with the LCD 16 showing a blank at the left hand side 11 and a "don't smoke" indicator on the right hand side 12. State 5a-120 handles the device in an off condition. If the user has a relapse, the user may choose to reenter the smoking cessation program by pressing the restart button and the device will restart at either the baselining phase or the withdrawal phase, depending on how long since they last used the device. However, in state 5-110 an attempt by the user to restart the program more than the allowed number of times will again result in an immediate transition to state 6-140.

Once no more restarts are allowed, the device is in a termination state, state 6-140. In this state, the LCD 16 is blank and all buttons are ignored making the device inoperative to the user.

FIG. 3 shows the major functional software/hardware components of the preferred exemplary embodiment. These same components could serve to implement many variations of the exemplary embodiment, and to implement totally different embodiments for a variety of human habitual behavior. The components are an executive control 220 and five major subgroupings: input management 208, sequence control 223, device activation 215, withdrawal management 231 and output management 239.

The executive 222 monitors and coordinates the overall operation of the device. Within the input management 208, the user input 210 is processed and categorized by the event processor 212 and relevant information is saved and summarized by the data collector 214. This data is then used to characterize the user and construct a tailored withdrawal program for the user. Many different variations of the data collector have been considered and several tested. These variations pertain to exactly what user data is collected and whether it's collected as raw data or as some descriptive statistic. Decisions are based on the nature of the habit being addressed, combined with empirical results in early use trials. For the exemplary embodiment, two variables are monitored: smoking rate and length of waking day. Smoking rate is measured by counting and recording the number of cigarettes smoked each day. This value is normalized with respect to day length by scaling it up to a value representing the expected number of smokes in a 24 hour period. Day length is measured by keeping a running average of the elapsed time between first and last device use each day. Possible variations in the data collector that are not now used include: tracking the minimum and maximum lengths of the user's waking day, and recording some indication of smoking pattern over time-of-day.

The sequence control 223, monitors elapsed time and other temporal cues in order to deduce relative time-of-day, day-of-week and to properly sequence the user through the various phases of the user's overall program. Relative time-of-day is managed by the time sequencer 228, based on regular signals from the system clock 230. Relative day-of-week is deduced by the day sequencer 226, based on the length of the current day and the amount of non-active time recorded. Unusual user activity such as excessively long periods of non-use or constant use of the device are detected and corrected. Decisions as to when to begin and end each of the major phases of the program are made by the phase sequencer 224.

Many variations of the sequence control have been considered and several tested. For example, the sequencing of time could be handled on a real time basis, with the user setting the time of day as with a conventional watch. For the current embodiment, it was considered beneficial to limit the number of user controls required. Therefore, a method was devised by which actual time of day was not needed. The current method uses only elapsed time and deduces when each new day begins, rather than basing daily transitions on real time. Daily transitions are important, since they are used to notify the user as to the number of days remaining in the current phase, and to determine the particular schedule of smokig events during the withdrawal phase. As indicated above, the current embodiment determines day transitions based on deduction. The day sequencer examines two parameters to make this deduction: (1) the elapsed time since the device as last used, and (2) the elapsed time since the current day began. Other variables could be used to vary or enhance this deduction. These two were chosen as a short and highly suggestive set. The first variable suggests whether or not the user has just completed a nightly sleep period. The second suggests whether the inactive period was actually a nightly sleep period, rather than a mid-day nap or non-use period. Variations that were considered but are not used in the current exemplary embodiment include: an additional switch which, when activated by the user, would indicate the start of a new day; having the user press the smoke button in some particular manner when they smoke the first cigarette each day (example, press the button twice in rapid succession); and simply starting a new day every 24 hours.

Within the device activation 215, the activation control 218 monitors and controls the on/off status of the device, based on power on/off signals 216, and controls initial start-up of the device permitting restarts via the system start/restart 220 request from the user.

Within withdrawal management 231, the personalized program generator 232 designs a withdrawal program tailored to each specific user based on data collected by the data collector. Many variations of the personalized program generator have been considered and some tested. The current preferred exemplary embodiment develops a personalized withdrawal program based on two variables: (1) the user's average delay between cigarettes during the baselining phase, and the average length of the user's waking day. Average consumption is calculated using a weighted average in order to determine central tendency without excessive distortion due to extreme data values. Many variations on the weighting scheme are possible, with the main intent being to use low weights with the extreme low and high data values and larger weights with more typical values. The present embodiment sorts the daily consumption values for the baselining phase in ascending order, then applies the following weighting factors: 0.0, 0.0, 0.25, 0.25, 0.25, 0.15, 0.1. These weights discard the two lowest values, discount the two highest values, and emphasize the three middle values. Variations to this weighted average approach that have been considered but are not now in use include: a simple arithmetic average, an average of those values falling within predetermined limits, and an average of the lowest and highest values.

The average waking day figure is calculated by the data collector directly. With a measure of consumption and the time period over which consumption occurs, the pesonalized program generator calculates the average delay between user smokes. This figure is used to classify the user into one of many user groups. Each group begins the withdrawal phase with essentially the same withdrawal schedule, which subsequently may be modified by the adaption processor to take into consideration observed variations within the group. The groups are defined by a tubular representation of a target withdawal curve. The target withdrawal curve represents the ideal withdrawal pattern for the user.

Figure 18:
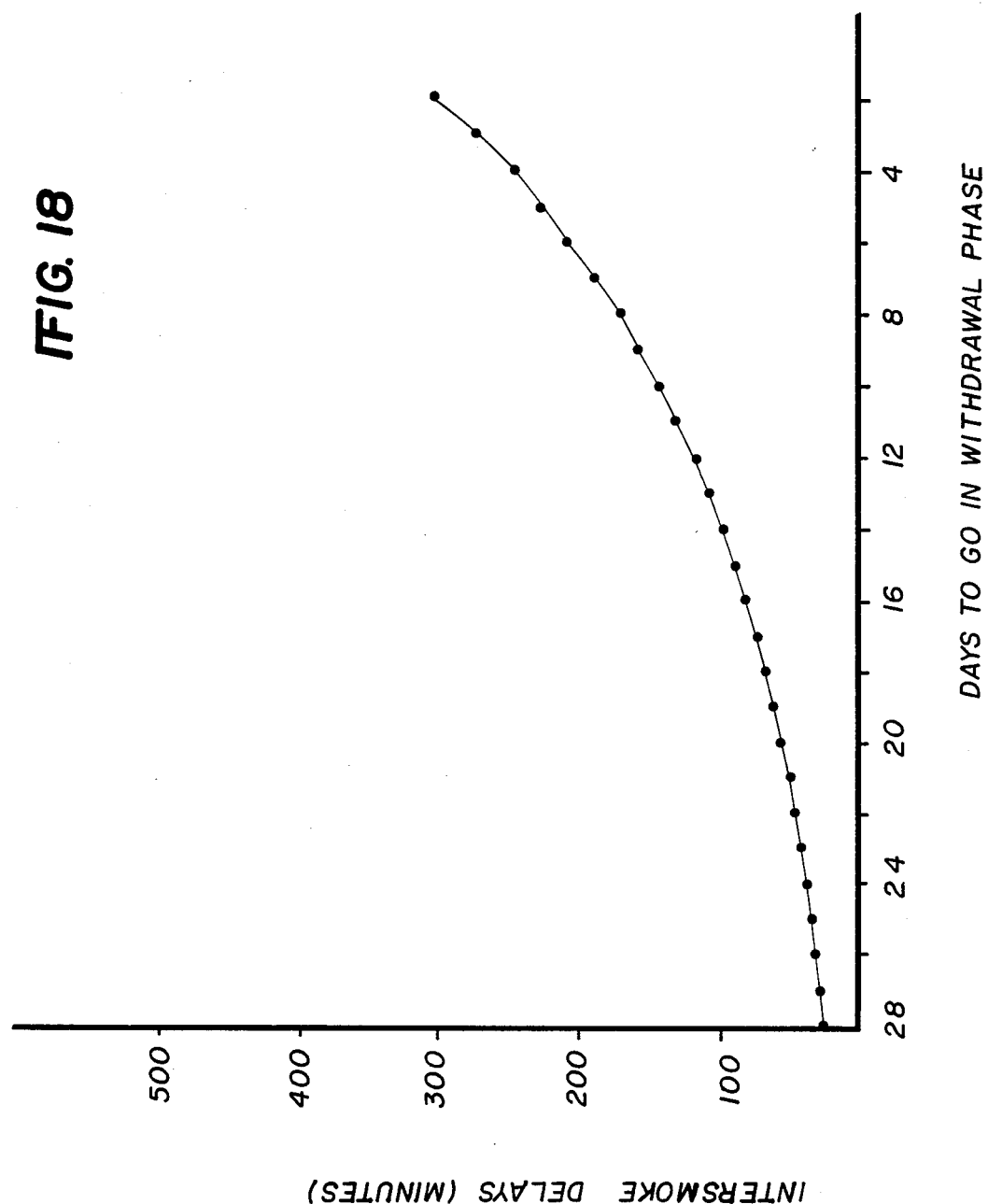
FIG. 18 is a graph of the programmed relationship between intersmoke delay times and the days remaining in the withdrawal phase.

Many different target withdrawal curves have been tried. The current embodiment uses one that is based on a combination of behavior modification theory, independent scientific studies of nicotine withdrawal, and our own empirical trials. FIG. 18 shows an example curve that depicts a gradual increase in the scheduled time between successive cigarettes over a 28-day withdrawal phase. The key points on this curve show the starting delay values for each of the 28 days in the withdrawal program. A table of these values defines a set of delay intervals associated with the number of days to go in the program. For example, at days 20 and 19 to go, the starting delay values are 53 and 58 minutes, respectively. A user whose calculated average delay falls between 53 and 58 minutes, would be designated in the user group that begins their withdrawal program with 20 days to go.

Based on the length of the user's smoking day and the starting days-to-go determined by the personalized program generator, the stimulus scheduler 234 plans specific times at which particular user stimuli are to be given. The scheduling algorithm has three major components: (1) when to have a user smoke the *first* cigarette each day, (2) when to have the user smoke the *last* each day, and (3) how to increase delays between successive smokes during each day. For determining the first cigarette, two basic approaches have been tested. In the first approach, the *user* is allowed to decide when to smoke the first cigarette each day. In the second approach, the stimulus scheduler uses a morning delay value for each day (called the AM Squeeze). Use of this squeeze accomplishes two purposes: (1) it enhances the stimulus control over the user's habit, and (2) it allows inter-cigarette delays to be shorter since the resulting smoking day is shorter. This second point is particularly important near the end of the withdrawal phase when only a small number of smoke events are scheduled for each day.

The preferred embodiment utilizes the AM squeeze, which is represented by a table of 28 morning delay values. Many variations of AM squeezes have been considered. The current embodiment uses values which increase according to a rule of constant percentage increase over time. Other possibilities include: no morning delays until the last 7 days of the program, at which point the morning delays are quite large and grow quickly; and an approach whereby the morning delay is a function of the observed morning delays actually effected by the user during the baselining phase.

For determining the *last* smoke event for each day, again two basic approaches are possible. With the first approach, the user can smoke as late into the day as wished. The user determines when to smoke the last cigarette. With the second approach, a daily curfew is determined and used to cut off scheduled smoke events after some specified time (called the PM Squeeze). The current embodiment uses the PM Squeeze in conjunction with the AM squeeze. A table of values define the target PM squeeze value for each day, which is used in conjunction with data on when the day started and the length of the user's average smoking day to define a curfew time for the day. The stimulus scheduler will not schedule the user's last cigarette too far into the curfew period, and will not schedule any additional smoke events once the curfew time has passed.

As with the AM squeeze, many variations are possible with the PM squeeze. Those considered include: use with the AM squeeze with no PM squeeze; use PM squeeze values which match the AM squeeze values; use PM squeeze values only during the end of the withdrawal phase; and use PM values which approximate AM values, but adjust them as required to maintain a smooth decrease in the number of scheduled smoke events each day. The last variation is the one employed in the current preferred exemplary embodiment.

In determining inter-smoke event delays during the day, several variations have been considerd and tested. One approach is to keep the delays constant, using whatever starting delay value is prescribed by the target withdrawal curve over and over during the day. Another approach begins by using the starting delay and increases it gradually over the day. Many methods of increasing the delay are possible. One such class of methods uses linear interpolation with the objective of increasing up to the next day's starting delay over some time period. The current embodiment increases linearly as a function of *time,* with the objective of reaching the next day's starting delay value in 24 hours. Other variations that have been considered include: linear increase as a function of time, but reaching the next day's starting delay value by the end of the user's waking day; linear increase as a function of the number of smoking events completed for the day; varying the rate of increase each day as necessary to obtain a desired smooth decrease in the number of scheduled smoke events each day; and several non-linear approaches (e.g., stair stepping functions).

The stimulus scheduler portion of the program offers a rich set of alternatives, with many possible combinations of first, last, and next smoke event scheduling algorithms. In addition to scheduling future stimulus events, the stimulus scheduler also schedules certain types of user feedback and instructions, and initiates *unscheduled* stimulus events in response to certain events and user actions. The scheduled feedback stimuli are intended to guide and instruct the user. The current exemplary embodiment, for example, displays icons on the LCD at various times during the program. These inform the user as to the current phase of operation, and whether or not they are presently allowed to smoke.

Many other scheduled informational and guidance feedback stimuli have been considered. Some are described below in the context of unscheduled stimuli, which occur in response to some event or user action. These unscheduled stimuli are intended to give the user feedback as to the possible effect of their actions on their habit modification program, to give them feedback on their progress with the program, or to provide instructions and encouragement as necessary to aid the user's progress. One category of such unscheduled stimuli are those given in response to a user action that is indicative of a problem. For example: the user may smoke *before* the next scheduled smoke event, a dieter may eat more than the prescribed number of calories for the day, or a user may not be maintaining the prescribed level of exercise. Many possible stimuli could be given the user to inform and aid them in improving.

The current exemplary embodiment utilizes a very simple form of such unscheduled stimuli. Each time the user presses the smoke button, an audible signal is given. The tone and duration of this signal is different depending on whether the smoke event occurred before or after the scheduled time. Other unscheduled stimuli considered for the exemplary embodiment, but not currently implemented, include: displays of the number of cigarettes smoked so far today, given at appropriate times as a reminder to the user; and displays of text whenever the user smokes off schedule, to serve as reminders and encouragement to return to the schedule.

Once the time for a scheduled stimulus event is reached, or the need for an unscheduled stimulus arise, the stimulus generator 236 provides the user with one or more specific stimuli (e.g., audio, visual, or vibrational). Many variations in stimuli are possible, including different sounds and music, text, pictures (fixed and moving), and touch sensitive stimuli such as different vibrations, heat, electrical current, and others. The current exemplary embodiment uses the following stimuli:
Audio:
    Melody segments at the start of each phase.

Two-frequency warble to signal scheduled smoke events.

Short beep to acknowledge button presses.

Somewhat longer and lower beep to acknowledge smoke button press associated with an early smoke.

Short melody to acknowledge device turn on.

Visual:
- Days-to-go in the current phase is always present in left-hand portion of the LCD.
- Time-to-next-schedule-smoke-event is always present in right-hand portion of the LCD, during the withdrawal phase.
- Current phase indicator is always present on the LCD.
- Smoke/No-Smoke icons, indicating whether or not the user can smoke, are always present on the LCD.

As the user follows a personalized withdrawal program, the adaptation processor 238 determines if any modifications to the personalized program are needed. For example, if the user seems unable to keep up with the program, the adaptation processor may slow the program down.

Many variations of the adaptation processor have been considered, and several tested. The general concept is to monitor the user's actions and adjust the scheduled program to best meet the specific user's needs. For example, if a dieter is having trouble keeping caloric intake within prescribed limits, the program may give special attention to more frequent feedback and encouragement to the user, and may alter the frequency of eating events and the guidance on types of foods to eat.

For exemplary embodiment, the main focus of the adaptation processor is to adjust the rate of withdrawal for the user that cannot keep up with the predetermined initially programmed rate. This is done by examining the user's record at the end of each day and deciding whether to repeat the same day's schedule or to move on to the schedule for the next day. The record that is examined involves the number of early smokes (i.e, smokes that occurred substantially before their associated scheduled smoke event).

Each smoke that occurs before its scheduled time is examined. The time remaining until the scheduled event is compared with the overall time between the last and next scheduled smoke events. If the early period exceeds a certain percentage of the overall time, then the smoke is considered an early smoke. The percentage threshold is a program parameter. A count of the number of early smokes is maintained, and at the end of the day is compared with the total number of actual smokes for the day. If the number of earlies exceeds a parameterized percentage of the total, then the day is repeated (i.e., the days-to-go value is not decremented, and the stimulus scheduler repeats the planned withdrawal pattern for that day again).

In this way, the user is given several attempts to make it through a particular level of withdawal difficulty before having to move to the next level. A limit on the number of repeats is imposed, however, so that users will not remain in the program indefinitely. Other variations considered include: no adaption at all, always move to the next day; and several schemes that back up time at various points which indicate user difficulty (e.g., when the user smokes their nth early smoke, immediately reduce the rate of withdrawal by backing up one or more days in the program).

Within output management 239, the output control 240 generates specific outputs requested by other components of the system. This could include audio signals produced by the audio source 242, visual images produced by the LCD display 244, or other types of stimuli produced by other output 246.

Figure 4:
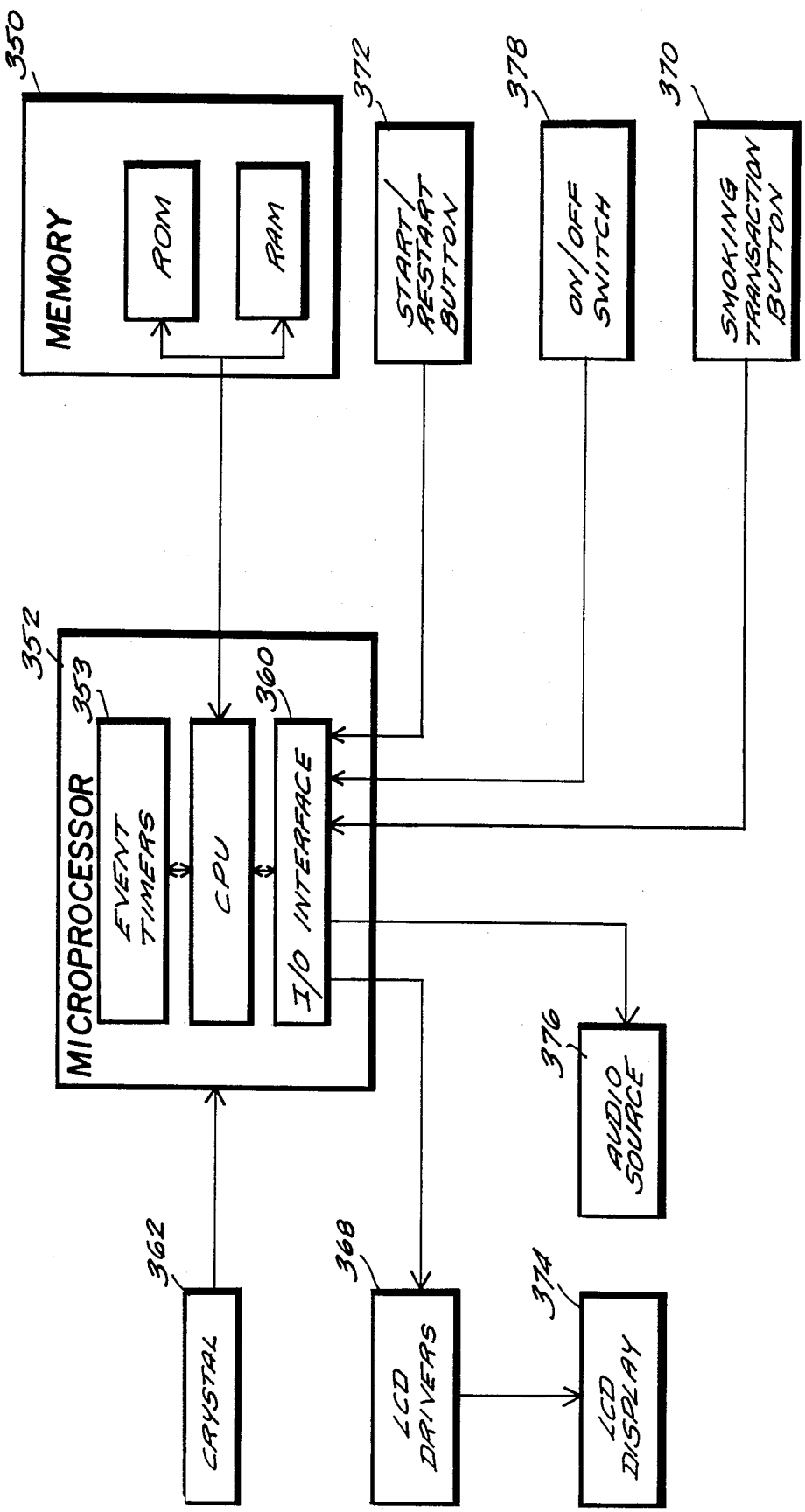
FIG. 4 is a schematic block diagram of the "hardware" components for the exemplary embodiment.

FIG. 4 shows a hardware block diagram for the preferred exemplary embodiment. The software program is stored in the ROM portion of memory 350 and executed by the microprocessor 352 to provide the functional controls just discussed with respect to FIG. 3.

The user input 210 is generated when the user presses the smoking transaction button 370 (smoke button 13) and thus generates an associated signal which is handled by the I/O interface 360. The event processor 212 and data collector 214 run as software programs and save needed user data in the ROM portion of memory 350.

As part of sequence control 223, the system clock is implemented using a crystal oscillator 362, and the event timers 353 on board the microprocessor 352. The event timer generates an interrupt once every minute which is processed by a software version of the time sequencer 228. The day sequencer 226 and phase sequencer 224 are also implemented using software programs stored in memory.

The power on/off signal 216 is generated by the on/off switch 378. The system start/restart signal 220 is generated by the start/restart button 372. When these are activated, specific signals are generated and processed by a software implementation of activation control 218.

The personalized program generator 232, stimulus scheduler 234, stimulus generator 236 and adaptation processor 238 are all implemented using software programs within the withdrawal management function 231.

The output control 240 is also implemented using a software program which sends data and control signals to/from the input/output interface 360 to the LCD drivers 368 and the audio source 376. The LCD drivers 368 then control the display of digits and other characteristics on the six digit LCD display 374.

Figure 5B:
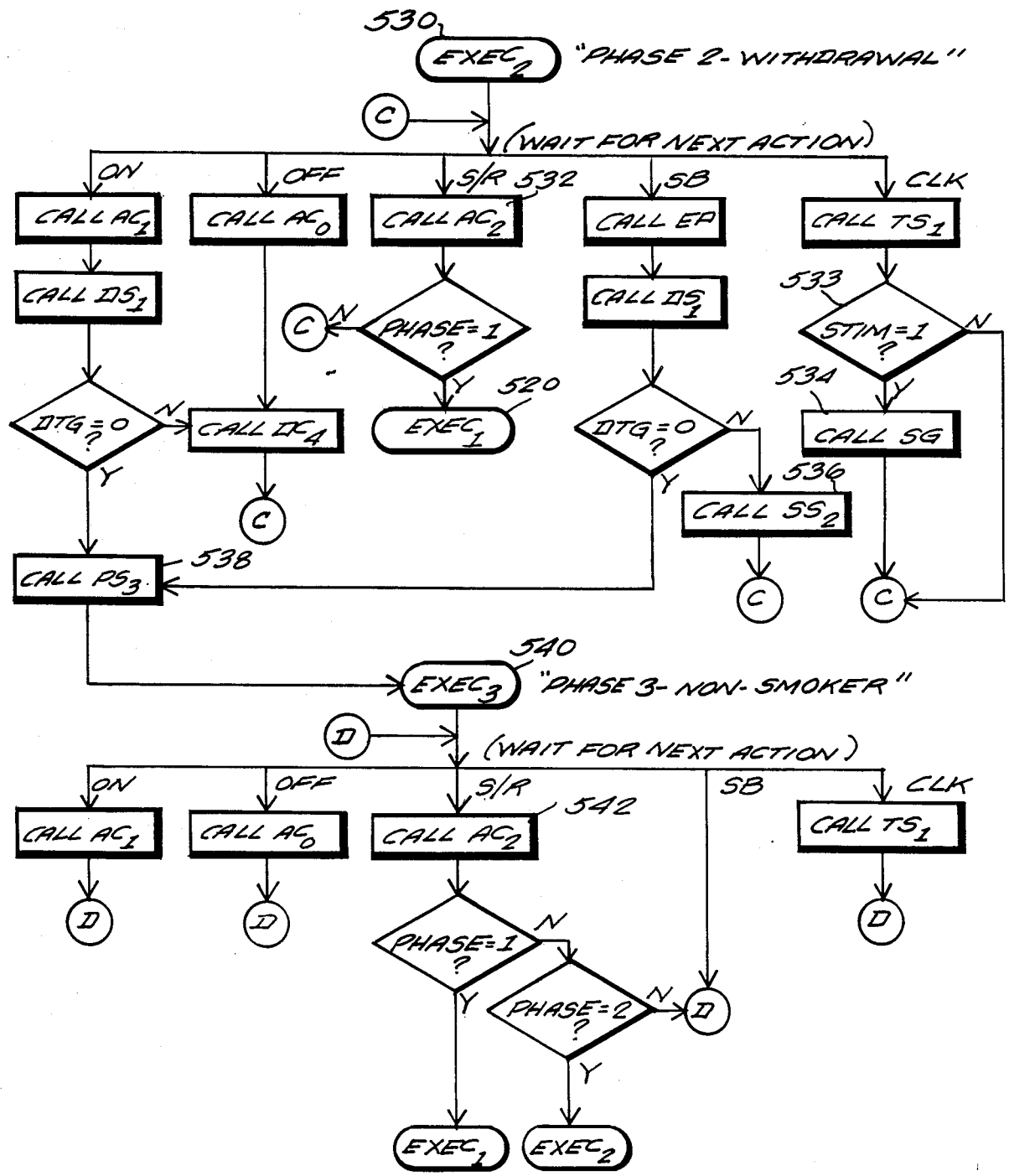

A more detailed description of the exemplary program is depicted by the flow chart of inter-related FIGS. 5–17. The basic executive routine is shown in FIGS. 5a and 5b. Start-up occurs at EXEC-0 (block 510).

At this point, several independent actions may occur. The flow chart shows the path taken for each possible action. If the user turns the device on, the "ON" path is taken, resulting in activation control subroutine AC-1 being called (block 511) followed by a return to the idle state, awaiting the next action. Similarly, if the user turns the device off, activation control subroutine AC-0 is called (block 512). If the user presses the smoke button (SB 514), or if a clock interrupt is received (CLK-515), no action is taken; and the program remains in the idle state. If the user presses the start/restart button (S/R), activation control subroutine AC-2 is called (block 513), and the program proceeds to the baselining phase at EXEC-1 (block 520).

Again in the baselining phase the program goes into an idle state, awaiting the next action. If the user turns the device on, activation control subroutine AC-1 is called (block 521), then the day sequencer subroutine DS-1 is called (block 525) to decide whether or not to begin a new day. The DTG value is checked, and until it reaches 0, data collection subroutine DC-4 is called (block 527) to keep track of user activity, and the program returns to the baselining phase idle state. Processing of the OFF and S/R actions are similar to that described for the EXEC-0 portion of the program, except that DC-4 is called to record user activity whenever the device is turned off. If the user presses the smoke button, the event processor (EP) is called (block 523) to record data about the smoke event; then the day sequencer subroutine DS-1 is called (block 526) to check if this user action occurred at the beginning of a new day; then DTG is checked to see (in case a new day was started) whether the baselining phase is complete. If not, the program returns to the idle state. If a clock interrupt occurs (CLK) the time sequencer subroutine TS-1 is called (block 524) to keep track of elapsed time. Once the baselining phase is completed, the DTG value will reach 0, and the personalized program generator (PPG) is called (block 528). Following this, the phase sequencer PS-2 is called (block 529) to start the withdrawal phase, which the program moves into at EXEC-2 (block 530).

The withdrawal phase begins at EXEC-2 (530) in an idle state. Processing of ON and OFF actions are similar to that described for the baselining phase (EXEC-1). If the user presses the start/restart button (S/R), activation control subroutine AC-2 is called (block 352) to decide at which phase to restart the program. If phase 1 is restarted, then the program moves to EXEC-1 (block 520). If phase 2 is restarted, the program remains in the withdrawal phase idle state. If the user presses the smoke button (SB), processing is similar to the baselining phase, with one major change: if DTG has not reached zero, the stimulus scheduler subroutine SS-2 is called (block 536) to schedule the stimulus signal for the next prescribed smoke event. If a clock interrupt (CLK) occurs, elapsed time is maintained by TS-1, and then if STIM-1, the stimulus generator is called (block 534) to produce the appropriate audio and visual stimulus directing the user to smoke. Once the prescribed number of days for the withdrawal phase are completed, DTG will reach 0, and the program will call the phase sequencer subroutine PS-3 (block 538) to begin phase 3 at EXEC-3 (block 540).

The non-smoker phase begins at EXEC-3 (block 540) in the normal idle state, awaiting the next action. The ON, OFF, and SB actions are essentially ignored. Clock interrupts (CLK) result in continuing to keep track of elapsed time. If the user presses the start/restart button (S/R), the activation control subroutine AC-2 is called (block 542) to determine whether or not to allow a restart, and if so, where to restart: either at phase 1 (EXEC-1) or phase 2 (EXEC-2).

Figure 6:
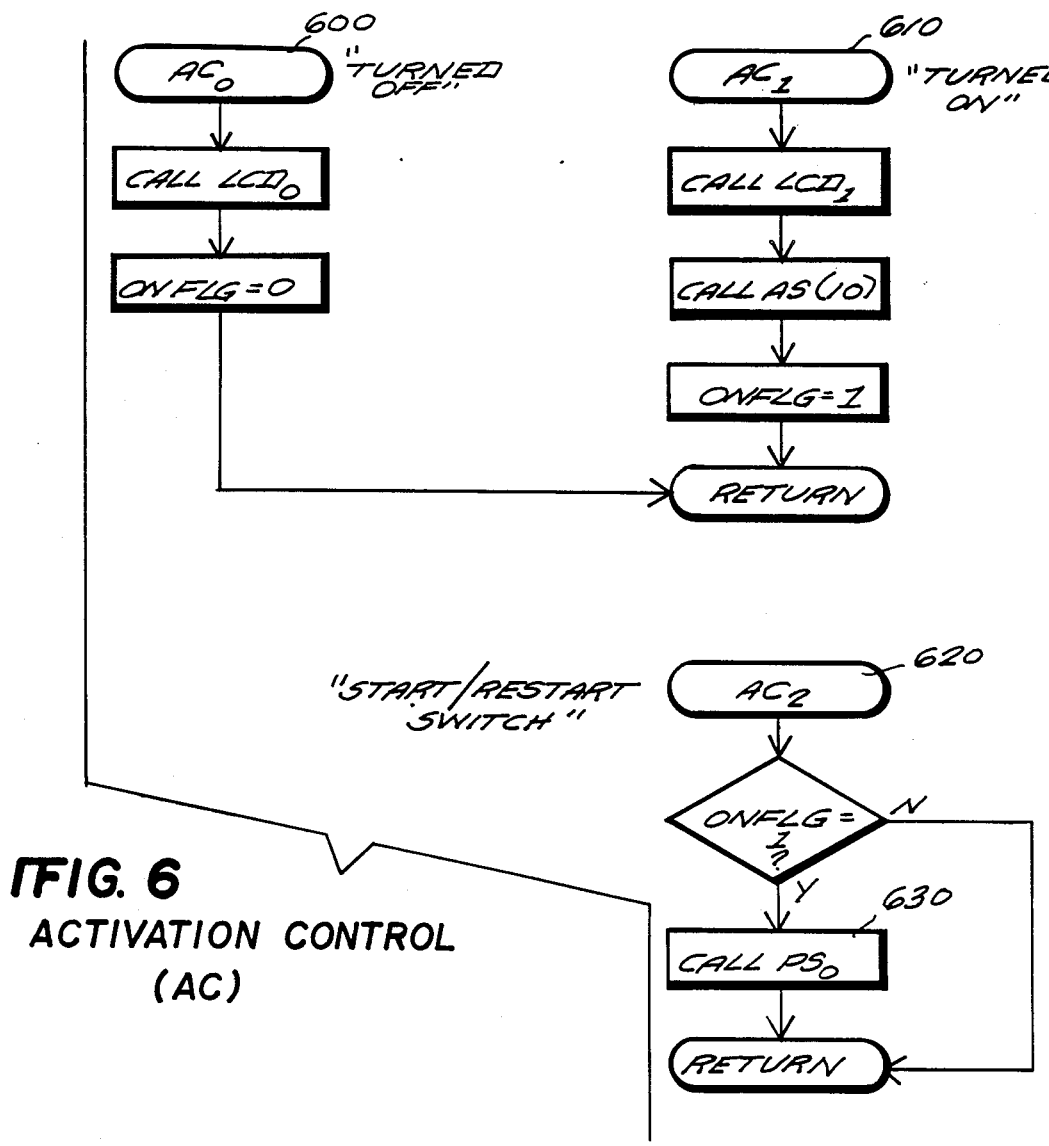

FIG. 6 shows the flow diagram of the activation control program (AC) starting with AC-0 (600) which processes the device being turned off, AC-1 (610) which processes the device being turned on, and AC-2 (620) which processes activation of the start/restart switch. For AC-2, if the device is on, the phase sequencer subroutine PS-0 is called (block 630) to decide whether or not to permit the restart and, if so, where to restart (phase 1 or 2).

FIGS. 7a and 7b show a program flow diagram for the phase sequencer (PS), consisting of four subroutines PS-0 through PS-3. PS-0 (700) is called to process a user request to restart the program. If the program is in phase 1, then control moves to PS-1 (720) to restart that phase. If not in phase 1, then the program checks the number of previous restarts (block 702). If the maximum number have already been permitted, then no restart is allowed. An audio signal indicating this is given (704) and the LCD display is set to show this (708). If the restart is allowed, the number of restarts is incremented (706). Next, the program calculates the amount of time since the last user action (710); and based on this, decides whether to restart at phase 1 or phase 2 (712). If phase 1 is restarted, control moves to PS-1 (720), where all phase 1 data variables are reinitialized (722), including TIME, which is reset to its original starting value. The data collector subroutine DC-1 is called to initialize a new day (724), the LCD display is set to show the days-to-go for phase 1 and that it's OK to smoke (726), and the audio signal subroutine is called to announce the restart (728). If phase 2 is restarted, control moves to PS-2 (730), where all phase 2 data variables are reinitialized, a new day is initialized, the LCD display is set for phase 2, and the restart is announced via the audio signal. Subroutine PS-3 (740) is called to start phase 3. It blanks the digit portions of the LCD display, indicates phase 3 has started, and displays the "don't smoke" icon (742), then gives a congratulatory audio signal (744).

Figure 8:
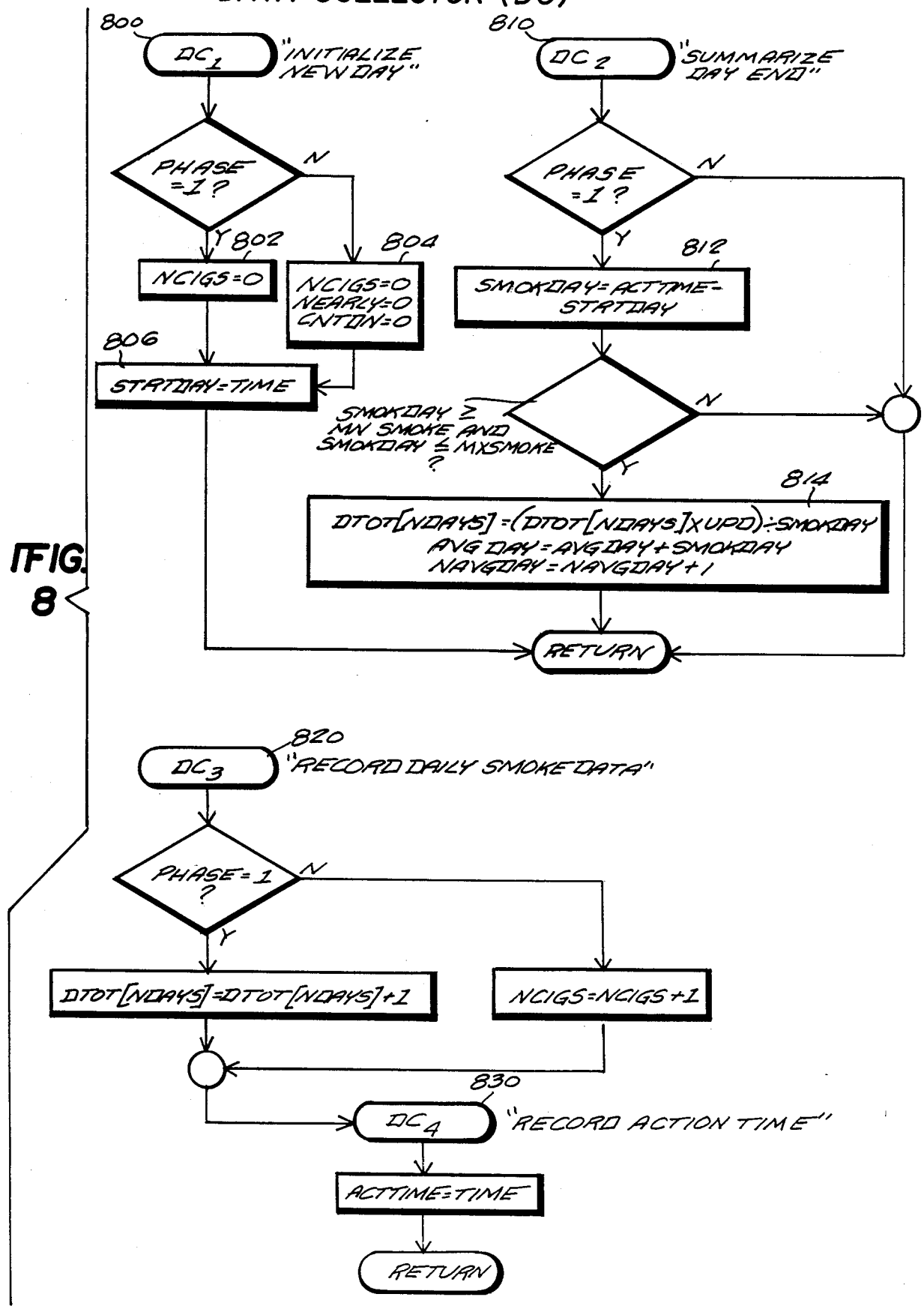

FIG. 8 shows a programming flow diagram for the data collector (DC), which consists of four subroutines, DC-1 through DC-4. DC-1 (800) initializes data for a new day by resetting count variables, depending on the phase (802 and 804), and records the time at which the day began (806). DC-2 (810) collects phase 1 summary data for the day just ended. It calculates the length of the user's active smoking day (812), and if this length is too short or too long, does not accept data for the day. If the length is within limits, the program normalizes the smoke count (DTOT) to a 24-hour day, and updates the average length of the user's smoking day (814). DC-3 (820) records daily smoking consumption counts as each day progresses. DC-4 (830) records the time of the most recent user action.

Figure 9:
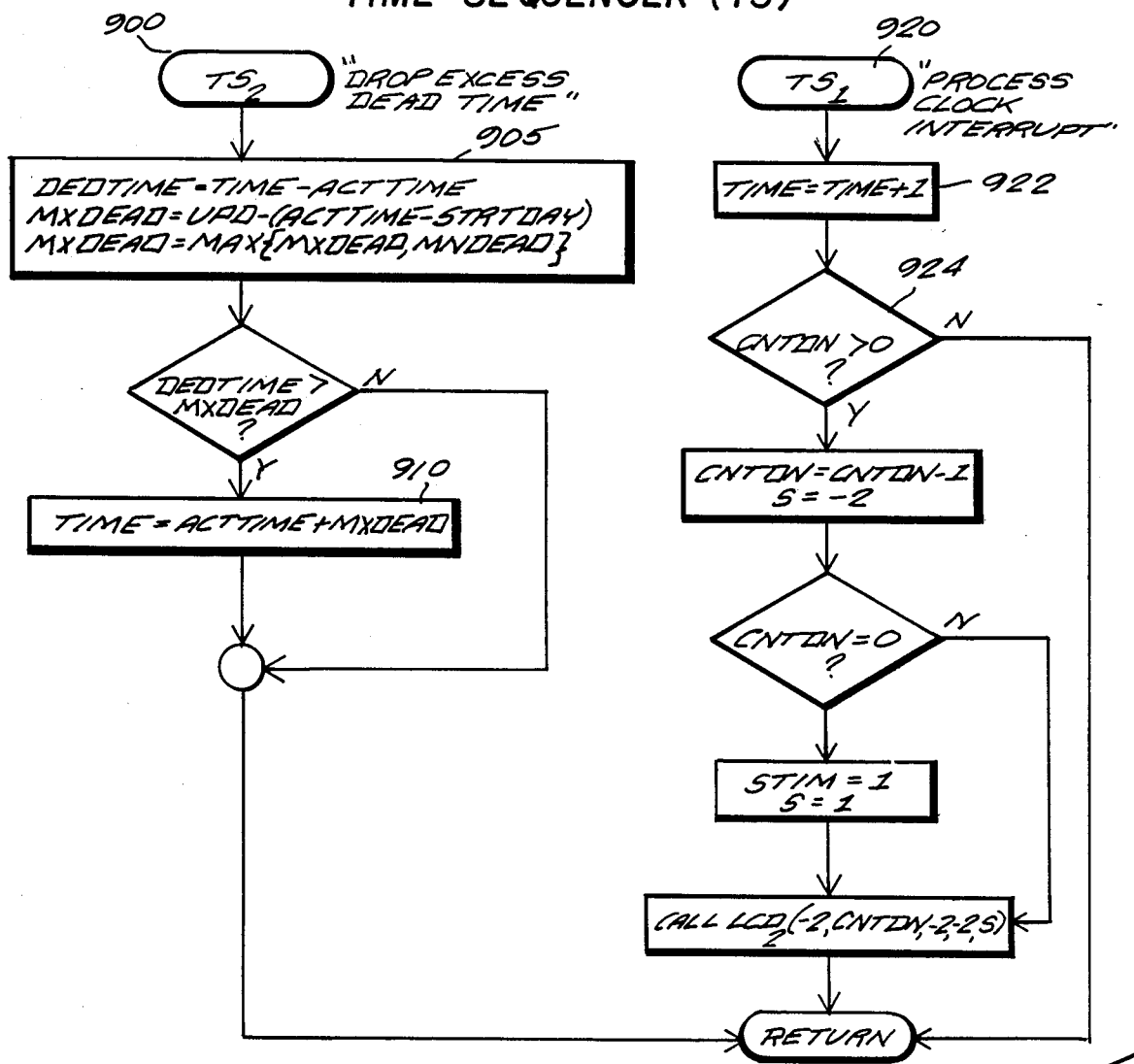

FIG. 9 shows a program flow diagram for the time sequencer (TS), which consists of three subroutines. TS-1 (920) processes clock interrupts. It maintains a software elapsed time record (922), and during phase 2 manages the countdown to the next scheduled smoke event. If the countdown has not already reached zero (924), it is decremented, and if the result is zero, a flag (STIM) is set to inform the Executive that it is time to generate a smoke event stimulus for the user (done in EXEC-2 at block 534). Finally, the LCD display is updated with the new countdown value and the appropriate smoking icon. TS-2 (900) checks for "dead time" (i.e., time during which the device has not been used), and if an excess amount has been found, it is disregarded by backing up time by an appropriate amount (910). TS-3 (930) is called to back up time by 1 day. This is done whenever a phase 2 day is repeated for the user.

FIG. 10 shows a program flow diagram for the day sequencer (DS), which consists of two subroutines. DS-1 (1000) checks to see if a new day has begun. It first eliminates any excess dead time (1010), then calculates the elapsed time since the current day started (1020), and finally determines if a new day appears to have started (1030). This determination is made by checking two conditions: (1) has the device been unused for at least some minimum amount of time that is likely to indicate a sleep period, and (2) is the current day long enough to likely be a full day. If both conditions are met, then it is assumed to be a new day, and control transfers to DS-2 (1040) to begin the new day. Data for the day just ended is summarized by calling DC-2 (1042). For phase 2, the adaptation processor is called (1044) to check if the user should repeat the schedule for the day just ended. If the RPTFLG is set, then TS-3 is called to back up time 24 hours (1047); otherwise, time remains as is and the day is advanced (1046). The data collector is called to initialize data for the new day (1048), and the LCD display is updated to show the new DTG value (1050 and 1052).

FIG. 11 shows a program flow diagram for the adaptation processor (AP), which consists of two subroutines. AP-1 (1100) proceses smoke events that occur early (i.e., before the scheduled time) to determine whether or not to treat them as a potential problem. For example, a smoke event that occurs only 2 minutes prior to a scheduled event that was scheduled 2 hours before, is not of concern. On the other hand, one that comes 1 hour early out of a scheduled 2-hour delay would be of concern. The subroutine determines the extent of earliness as a percentage of the scheduled delay between the previous and next events (1102). If this percentage exceeds a threshold (1104), a special audio acknowledgement signal is given (1106), and a count of the number of early events is updated (1110). If the threshold is not exceeded, the normal acknowledgement signal is given (1108). AP-2 (1120) determines at the end of each day whether or not the day should be repeated due to an excessive number of early smoke events. The extent of early events is calculated as a percentage of the total number of smoke events for the day (1122). If this percentage exceeds a threshold (1124), a count of the total number of day repeats during phase 2 is updated (1126), and if this count does not exceed a maximum (1128), a flag is set to inform the day sequencer to repeat the day (see DS-2 block 1045).

FIG. 12 shows a program flow diagram for the event processor (EP 1200), which processes smoke button presses. If the device is OFF (1202), no action is taken. Otherwise, phases 1 and 2 are processed appropriately. For phase 1, an audio acknowledgement of the button press is given (1204), and the data collector is called to record pertinent data (1212). For phase 2, if this is the very last smoke event (i.e., DTG=1), the phase is completed and DTG is set to zero to inform the executive of this (1203). Otherwise, the countdown to the next smoke event is tested (1206); and if it's still counting down, the adaptation processor is called to deal with the early event (1210). If the countdown has stopped, an acknowledgement of the button press is given (1208), and in both cases pertinent data is recorded (1212).

FIG. 13 shows a program flow diagram for the personalized program generator (PPG (1300)), which processes data collected in phase 1 and generates a personalized withdrawal schedule for the user. The average duration of the user's waking day is calculated, and this is used to set a control variable used by the day sequencer during phase 1 (1302). A statistical measure of the user's smoking consumption during phase 1 is obtained by sorting the daily smoke counts (1304) and computing a weighted average of these sorted values (1306). The weighted average is designed to provide a measure of central tendency that is not overly distorted by unusually low or high values for a small number of days. A normalized measure of the average time between smokes is calculated (1308) and used to determine the user's starting point on the stored withdrawal curve (1310). This is done by comparing the user's intercigarette delay value with a table of such values, where the interpolated position of the user's value within the table defines the number of days required for phase 2. This in turn is used to determine the scheduled smoke events for each day as phase 2 progresses.

Figure 14B:
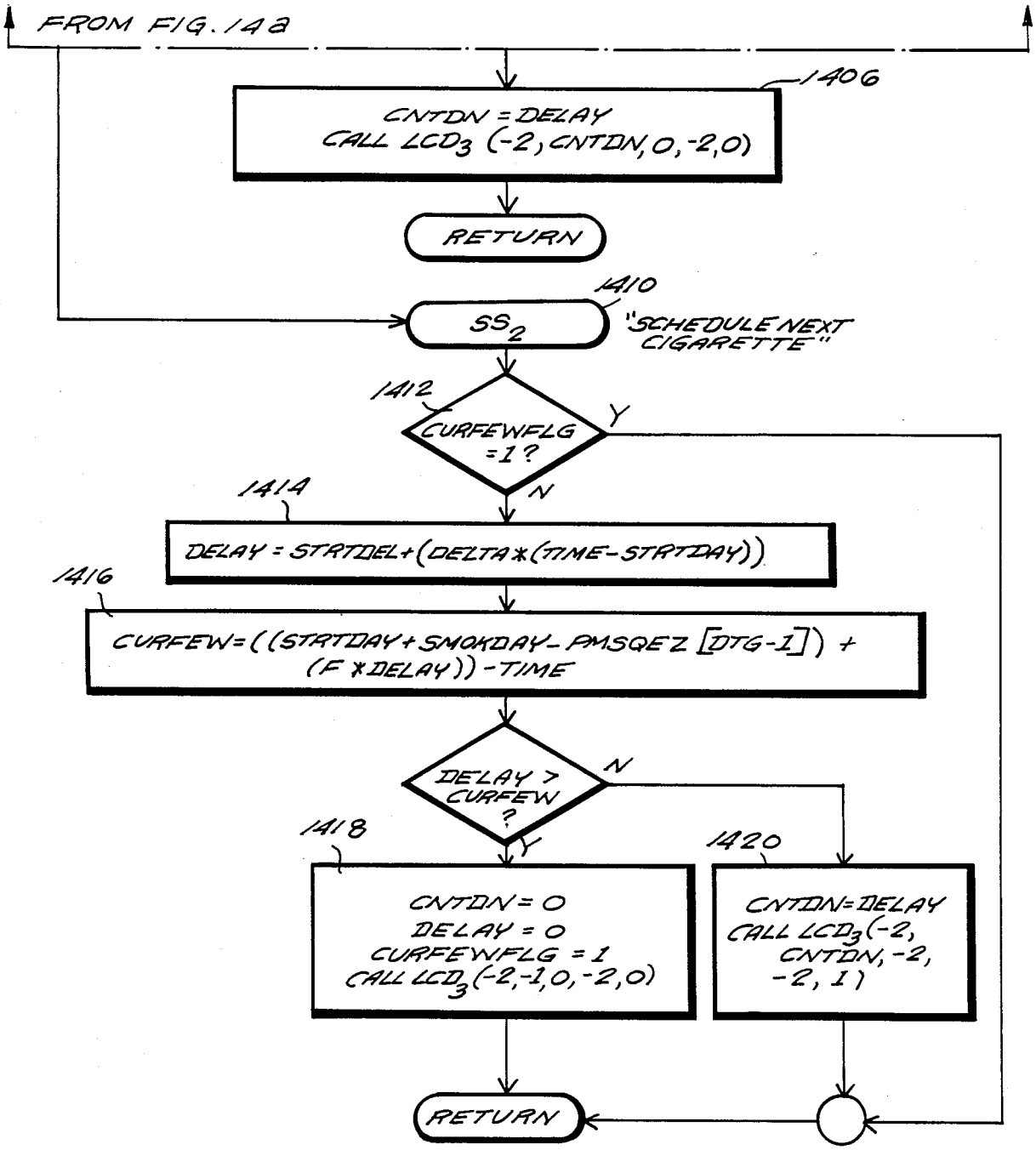

FIG. 14 shows a program flow diagram for the stimulus scheduler (SS), which consists of two subroutines. SS-1 (1400) schedules the user's first smoke event each day. Delay values from the withdrawal curve are determined for the current and next day, and a slope value for intra-day interpolation of the withdrawal curve is computed (1401). If the device has been left on during the user's sleep period (1402), then no special first-smoke scheduling is done, and control moves to SS-2 for scheduling. If the device was off during sleep, then the initial delay value for the current day is read from a table (1404). The countdown timer is set to schedule the next smoke event and the LD display is updated accordingly (1406). The subroutine SS-2 (1410) schedules the next smoke event for the day. If the daily curfew period is in effect (1412), no additional smoke event is scheduled. Otherwise, the next delay value is calculated using linear interpolation based on time of day (1414). The required curfew cutoff time for the day is calculated, using a grace period based on the length of the next delay (1416); and if the next delay falls beyond the curfew time, no additional smoke event is scheduled, and the LCD display is updated appropriately (1418). If the next delay is acceptable, the countdown timer is set and the LCD display updated to show a countdown to the event (1420).

FIG. 15 shows a program flow diagram for the stimulus generator (SG (1500)), which generates the audio and visual stimuli directing the user to smoke. The audio source is called to produce the appropriate sound (1502); the LCD display is updated appropriately (1504), and a flag is reset (1506) to inform the executive that the last scheduled stimulus has been given (see EXEC-2 block 533).

Figure 16:
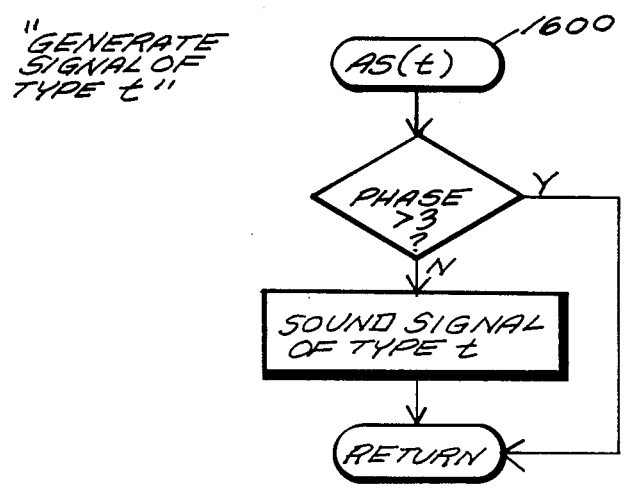

FIG. 16 shows a program flow diagram for the audio source (AS (1600)), which generates various audio signals during phases 1,2 and 3. Once the program completes phase 3, no signals are given. Possible signals include: a "beep" acknowledging a button press, a "warble" signal serving as a smoke stimulus, and a short melody used to announce the start of each phase.

Figure 17B:
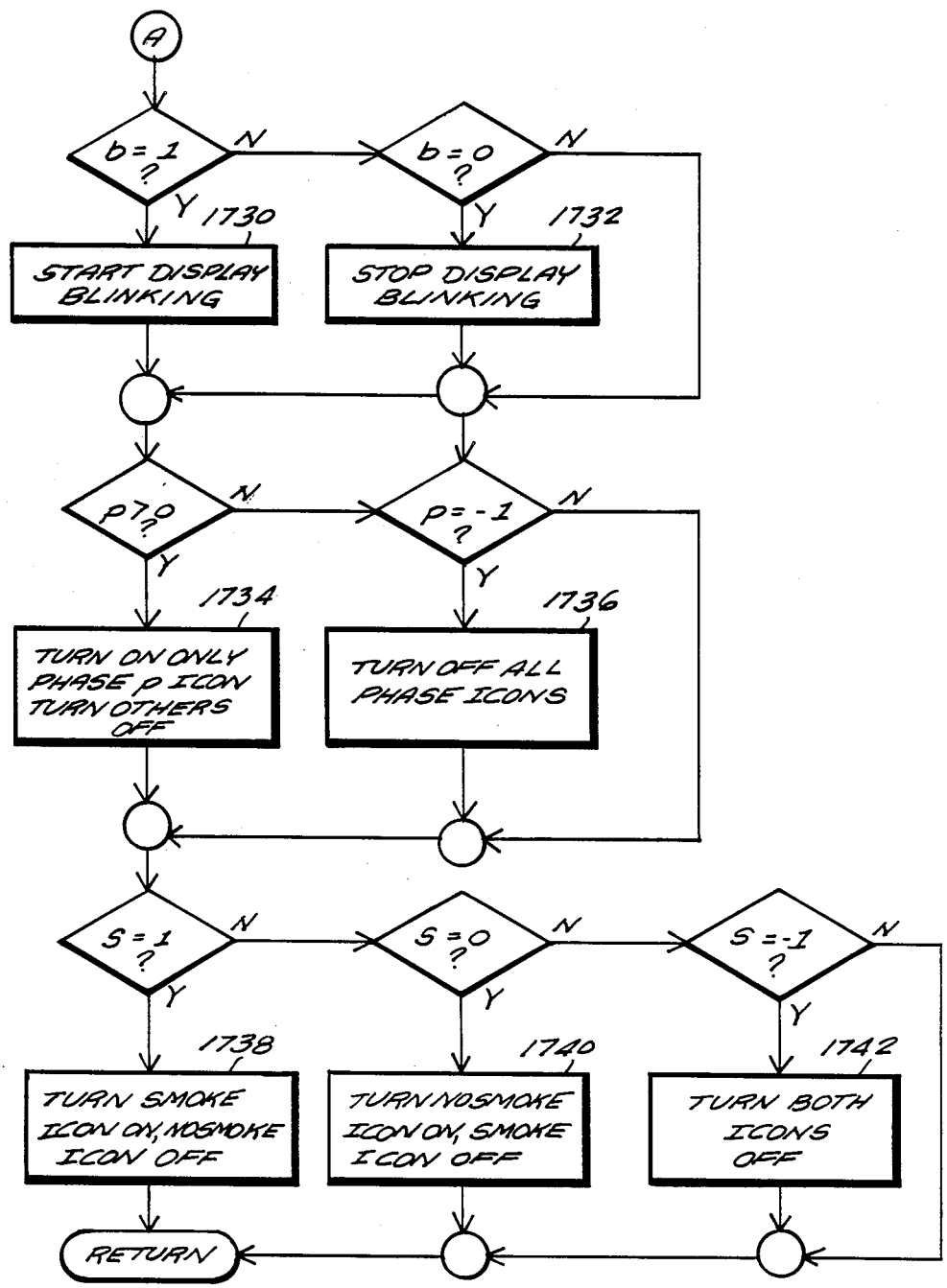

FIG. 17 shows a program flow diagram for the liquid crystal (LCD), which consists of three subroutines. LCD-0 (1700) turns the display off. LD-1 (1710) turns the display on, without affecting the display contents. LCD-2 (1720) sets the contents of the display, independent of its on/off state. If the left-hand display value is zero or greater, it is converted to a 2-digit decimal value (1722) and sent to the display hardware (1724). If the value is −1, the left-hand display is blanked (1726). Otherwise, the left-hand display is left unchanged. The right-hand display is treated similarly, except that a non-negative value is converted to a 3-digit value representing hours and minutes (1728). If argument b=1, the display is set to blink (1730); if b=0, the display is set to not blink (1732); otherwise, the blinking state is unaffected. If the argument p is greater than zero, the icon symbol for phase p is turned on, and all other phase icons are turned off (1734). If p=1, all phase icons are turned off (1736); otherwise, the phase icons are unaffected. If the argument s=1, an icon indicating it's OK to smoke is turned on, and its companion icon is turned off (1738); if s=0, an icon indicating that the user should not smoke is turned on, and its companion icon is turned off (1740); if s=1, both smoke icons are turned off (1742); otherwise, the smoke icon state is unaffected.

FIGS. 5-17 collectively define a selfexplanatory flow chart of the exemplary software package embedded in memory 350. The meanings of the somewhat abbreviated mnemonic subroutine names and exemplary values for the fixed parameters used in the flow chart are tabulated below:

EXEC=the EXECutive portion of the software, with subscripts 0,1,2,3 being used for different interval segments.
A,B,C,D=connector points within a program
AC=Activation Control with associated subscripts for identifying the different individual subroutines.
PS=Phase Sequencer with associated subscripts for identifying the different individual subroutines.
DC=Data Collector with associated subscripts for identifying the different individual subroutines.
TS=Time Sequencer with associated subscripts for identifying the different individual subroutines.
DS=Day Sequencer with associated subscripts for identifying the different individual subroutines.
AP=Adaption Processor with associated subscripts for identifying the different individual subroutines.
EP=Event Processor subroutine
PPG=The Personalized Program Generator subroutine
SS=Stimulus Scheduler with associated subscripts for identifying different individual subroutines.
SG=Stimulus Generator subroutine
AS=Audio Source subroutine
LCD=Liquid Crystal Display with associated subscripts for identifying the different individual subroutines.
P1LEN=7
TIMZERO=0
MINDAY=Set to 1080 for phase 1, and calculated for phase 2.
MNDEAD=Set to 180 for phase 1, and calculated for phase 2, as 60% of the user's average sleep time.
UPD=1440
MNSMOKE=300
MXSMOKE=1440
MAXRS=1
F=20
MXERLTPC=10
MXERLNPC=20
MXRPTS=10
MNDAYPC=100
WT=0,0,25,25,25,15,10
SD=330,330,272,247,225,204,186,168, 153,139,126,115,104,95,86,78,71, 64,58,53,48,44,40,36,33,30,27,25
AMSQEZ=480,330,313,297,281,265,250,236, 221,207,193,180,166,153,141,128, 116,104,93,82,70,60,49,39,29,19, 9,0
PMSQEZ=480,330,408,222,294,168,240,150, 72,1568,120,84,60,60,60,60,0,0,0, 0,0,0,0,0,0,0,0

Although only one exemplary embodiment has been described in detail, those in the art will recognize that many modifications and changes (including programming changes, parameter value changes, and hardware component changes) may be made in the exemplary embodiment while yet retaining many of the novel features and advantages of this invention. Accordingly, all such modifications and variations are to be included within the scope of the appended claims.

What is claimed is:

1. A smoking reduction method for scheduling time intervals between active inducement of user smoking events so as to gradually reduce a user's smoking habit, said method comprising:
   tracking errant smoking event occurrences of the user with respect to said scheduled time intervals;
   establishing and generating a user adaptive withdrawal schedule which schedules and displays the time intervals between permitted smoking events over a plurality of days and in response to said errant smoking event occurrences; and
   visually indicating to the user the number of days left to go in said schedule.

2. A smoking-reduction system for scheduling time intervals between active inducement of user smoking events so as to gradually reduce a user's smoking habit, said system comprising:
   means for tracking errant smoking event occurrences of the user with respect to said scheduled time intervals;
   modification programming means for establishing and generating a user adaptive withdrawal schedule which schedules and displays the time intervals between permitted smoking events over a plurality of days and in response to said errant smoking event occurrences; and
   display means which includes a visual display indicating the number of days left to go in said schedule.

3. Apparatus for stimulating human behavior modification, said apparatus comprising:
   event sensor means for generating an event signal representing the occurrence of a discrete event associated with a predetermined pattern of habitual human behavior;
   modification programming means connected to receive said event signals over a predetermined first time span during which the habitual behavior naturally occurs and to responsively generate a personalized program for modification of said habitual behavior including a programmed schedule of future occurrence times for said events to occur over a second time span; and
   output means connected to output a humanly sensible stimulus at said scheduled future occurrence times;
   wherein said modification programming means includes means for detecting during the second time span whether the event signals accurately follow the established programmed schedule of future occurrence times and, if not, for adaptively changing said programmed schedule of future occurrence times in response to detected deviations.

4. Apparatus as in claim 3 including further output means which includes, during the second time span, a visible indicator of the time remaining until the next scheduled event occurrence time.

5. Apparatus as in claim 3 wherein said output means includes a visible indicator of the time remaining in a least one of said first and second time spans.

6. Apparatus as in claim 3 wherein said output means comprises an audio transducer.

7. Apparatus as in claim 3 wherein:
   said event sensor means comprises at least one manually activated electrical switch;
   said output means comprises audio and visual electrotransducers; and
   said modification programming means comprises a microprocessor based data processor including a digital memory and connected to receive inputs from the event sensor means and to responsively drive said output means in accordance with a predetermined computer control program stored in said digital memory.

8. A method for evoking personalized modification of a human behavior denoted by behavioral events, by use of a programmable device with which a user interacts to create and implement a behavior modification plan, said method comprising:
- user-activating said programmable device upon the occurrences of said behavioral events;
- establishing an unmodified behavior baseline during a first predetermined period of time by recording the occurrences and times of at least one of said behavioral events during said first period;
- automatically establishing a behavior modification plan in accordance with a predetermined programmed algorithm stored in said device including:
  - (i) establishing a second period of time for modifying said behavior;
  - (ii) establishing the timing intervals of said behavioral events which said person is to be permitted to commit during said second period;
- signaling the user via said device, by at least one stimulus, so that the user is prompted to commit said permitted behavioral events at said timing intervals during said second period;
- user-activating said device at the time when said permitted behavioral event is actually committed; and
- revising said timing between said permitted behavioral events during said second period if the user records the commission of behavioral events with timing that substantially differs from said behavior modification plan.

9. A method according to claim 8 wherein said behaviorism is habitual smoking.

10. Apparatus for evoking modification of a predetermined human behavior, said behavior being denoted by a time sequence of behavioral events, by use of a programmable device with which a person interacts to create and implement a behavior modification time period, said apparatus comprising:
- means for activating said programmable device upon the occurrences of said events;
- means for establishing an unmodified behavior base line during a first predetermined period of time by recording the occurrences and timing of at least one of said first behavioral events during said period;
- means for establishing a behavior modification plan including
  - (1) means for establishing a modification period of time for modifying said behaviorism,
  - (ii) means for establishing the future timing intervals of said behavioral events which said person is permitted to commit during said modification period;
- means for informing the user via said device, of said established future timing of said behavioral events which said person is permitted to commit during said modification period; and
- means for revising said future timing intervals if the user commits behavioral events in a manner substantially differing from the behavior modification plan.

11. A smoking reduction system for scheduling time intervals between user smoking events so as to gradually reduce a user's smoking habit, said system comprising:
- a smoke event sensor means for generating an event signal representing occurrence of an actual user smoking event;
- timing means for generating a personalized program gradually increasing future time intervals between said smoking events including a programmed schedule of future smoking event occurrence times;
- output means connected to signal a user at scheduled future smoking event occurrence times; and
- program adaptation means, responsive to a comparison of the timing of actual smoking events and scheduled smoking events over a period of time, for temporarily suppressing further increased time intervals between future scheduled smoking events.

12. A smoking reduction system as in claim 11 wherein said timing means generates day-by-day schedules for future smoking events and wherein said program adaptation means includes means for repeating the current or an earlier day's schedule in response to detecting an excessive number of actual smoking events occurring substantially prior to scheduled occurrence times.

13. A smoking reduction system for scheduling time intervals between user smoking events so as to gradually reduce a user's smoking habit, said system comprising:
- a smoke event sensor means for generating an event signal representing occurrence of an actual user smoking event;
- timing means for generating a personalized daily program of future timing intervals between said smoking events including a programmed daily schedule of future smoking event occurrence times;
- said timing means including means for deducing a user's probable personal daily waking and sleeping pattern and for generating such daily future smoking event occurrence times as a function of the relative time within such waking and sleeping pattern;
- output means connected to signal a user at scheduled future smoking event occurrence times; and
- an on/off switch connected to said means for deducing for activation by the user in correspondence with the user's waking/sleeping pattern.

14. A smoking reduction system as in claim 13 wherein said means for deducing the user's waking and sleeping pattern is further responsive to the occurrence of time periods during which no event signals are generated.

15. A smoking reduction system for scheduling time intervals between user smoking events so as to gradually reduce a user's smoking habit, said system comprising:
- a smoke event sensor means for generating an event signal representing occurrence of an actual user smoking event;
- timing means for generating a personalized daily program of future timing intervals between said smoking events including a programmed daily schedule of future smoking event occurrence times;
- said timing means including means for deducing a user's probable personal daily waking and sleeping pattern and for generating such daily future smoking event occurrence times as a function of the relative time within such waking and sleeping pattern; and output means connected to signal a user at scheduled future smoking event occurrence times;

said means for deducing the user's waking and sleeping pattern being responsive to the occurrence of time periods during which no event signals are generated.

16. (Amended) A smoking reduction system as in claim 11, 12, 13, 15 or 14 further comprising:

restart means for restaring the schedule, when activated, for a predetermined limited number of restarts.

17. A smoking reduction method for scheduling time intervals between user smoking events so as to gradually reduce a user's smoking habit, said method comprising:

generating an event signal representing occurrence of an actual user smoking event;

generating a personalized program of future time intervals between said smoking events including a programmed schedule of future smoking event occurrence times;

signalling a user at scheduled future smoking event occurrence times; and temporarily suppressing further changes in the time intervals between future scheduled smoking events responsive to a comparison of the timing of actual smoking events and scheduled smoking events over a period of time.

18. A smoking reduction method as in claim 17 wherein said generating step generates day-by-day schedules for future smoking events and wherein said temporarily suppressing step includes repeating the current or an earlier day's schedule in response to detecting an excessive number of actual smoking events occurring substantially prior to scheduled occurrence times.

19. A smoking reduction method for scheduling time intervals between user smoking events so as to gradually reduce a user's smoking habit, said method comprising:

generating an event signal representing occurrence of an actual user smoking event;

generating a personalized daily program of future timing intervals between said smoking events including a programmed daily schedule of future smoking event occurrence times;

deducing a user's probable personal daily waking and sleeping pattern and using such daily pattern to vary the daily schedule of future smoking event occurrence times as a function of the relative time within such waking and sleeping pattern;

signaling a user at scheduled future smoking event occurrence times; and including use in said deducing step of an on/off switch activated by the user in correspondence with the user's waking/sleeping pattern.

20. A smoking reduction method for scheduling time intervals between user smoking events so as to gradually reduce a user's smoking habit, said method comprising:

generating an event signal representing occurrence of an actual user smoking event;

generating a personalized daily program of future timing intervals between said smoking events including a programmed daily schedule of future smoking event occurrence times;

deducing a user's probable personal daily waking and sleeping pattern and using such daily pattern to vary the daily schedule of future smoking event occurrence times as a function of the relative time within such waking and sleeping pattern; and signaling a user at scheduled future smoking event occurrence times;

wherein said deducing step is responsive to the occurrence of time periods during which no event signals are generated.

21. A smoking reduction method as in claim 17, 18, 19 or 20 further comprising the step of:

restarting the schedule when requested by a user but only for a predetermined limited number of restart request.

22. A smoking reduction system for scheduling time intervals between user smoking events so as to gradually reduce a user's smoking habit, said system comprising:

a smoke event sensor means for generating an event signal representing occurrence of an actual user smoking event;

timing means for generating a personalized daily program of future timing intervals between said smoking events including a programmed daily schedule of future smoking event occurrence times;

said timing means including means for deducing a user's probable personal daily waking and sleeping pattern from activation of an on/off switch of a device for recording said event signals and from the occurrence of time periods during which no smoke event signals are generated and for generating such daily future smoking even occurrence times as a function of the relative time within such waking and sleeping pattern; and output means connected to signal a user at scheduled future smoking event occurrence times.

23. A smoking reduction method for scheduling time intervals between used smoking events so as to gradually reduce a user's smoking habit, said method comprising:

generating an event signal representing occurrence of an actual user smoking event;

generating a personalized daily program of future timing intervals between said smoking events including a programmed daily scheduled of future smoking events occurrence times;

deducing a user's probable personal daily waking and sleeping pattern and using such daily pattern from activation of an on/off switch of a device for recording said event signals and from the occurrence of time periods during which no smoke event signals are generated to vary the daily schedule of future smoking event occurrence times as a function of the relative time within such waking and sleeping pattern; and signaling a user at scheduled future smoking event occurrence times.

24. Apparatus for stimulating human behavior modification, said apparatus comprising:

event sensor means for generating an event signal representing the occurrence of a discrete event associated with a predetermined pattern of habitual human behavior;

modification programming means connected to receive said event signals over a predetermined first time span during which the habitual behavior naturally occurs and to responsively generate a personalized program for modification of said habitual behavior including a programmed schedule of future occurrence times for said events to occur over a second time span; and output means connected to output a humanly sensible stimulus at said scheduled future occurrence times;

wherein said modification programming means includes means responsive to operator request for recycling said program means for a predetermined number (at least one) of reuse cycles but which is thereafter rendered incapable of further reuse.

25. A method for evoking personalized modification of a human behavior denoted by behavorial events, by use of a programmable device with which a user interacts to create an implement a behavior modification plan, said method comprising:

user-activating said programmable device upon the occurrences of said behavioral events;

establishing an unmodified behavior baseline during a first predetermined period of time by recording the occurrences and times of at least one of said behavioral events during said first period;

automatically establishing a behavior modification plan in accordance with a predetermined programmed algorithm stored in said device including:
(i) establishing a second period of time for modifying said behavior;
(ii) establishing the timing intervals of said behavioral events which said person is to be permitted to commit during said second period;

signaling the user via said device, by at least one stimulus, so that the user is prompted to commit said permitted behavioral events at said timing intervals during said second period; and repeating all the above-stated steps upon request by the user but only for a predetermined limited number of restart requests.

26. Apparatus for stimulating human behavior modification, said apparatus comprising:

event sensor means for generating an event signal representing the occurrence of a discrete event associated with a predetermined pattern of habitual human behavior;

modification programming means connected to receive said event signals over a predetermined first time span during which the habitual behavior naturally occurs and to responsively generate a personalized program for modification of said habitual behavior including a programmed schedule of future occurrence times for said events to occur over a second time span;

output means connected to output a humanly sensible stimulus at said scheduled future occurrence times; and means for generating on-off signals representing the waking/sleeping schedule of the user and wherein said modification programming means is connected to use the schedule of said on-off signals in generating said programmable schedule of future occurrence times.

27. Apparatus as in claim 26 wherein said modification programming means ignores event signals occurring during apparent waking/sleeping schedules corresponding to unusually short or long days during said first predetermined time span.

28. Apparatus as in claim 26 wherein said modification programming means ignores unusually long periods of inactivity in said event signals and on/off activations.

29. Apparatus as in claim 26 wherein said modification means also schedules recurrent curfew periods during which no events are scheduled to occur, determined as a function of detected on-off times and wherein said output means includes a visible indicator of the existence of such a curfew period.

30. Apparatus for stimulating human behavior modification, said apparatus comprising:

event sensor means for generating an event signal representing the occurrence of a discrete event associated with a predetermined pattern of habitual human behavior;

modification programming means connected to receive said event signals over a predetermined first time span during which the habitual behavior naturally occurs and to responsively generate a personalized program for modification of said habitual behavior including a programmed schedule of future occurrence times for said events to occur over a second time span; and output means connected to output a humanly sensible stimulus at said scheduled future occurrence times;

wherein said modification programming means includes means for also initiating at least one uniquely distinquishable further humanly sensible stimulus via said output times significantly different than said scheduled occurrence times.

31. Apparatus for actively stimulating human behavior modification, said apparatus comprising:

event sensor means for generating an event signal representing the occurrence of a discrete event associated with a predetermined pattern of habitual human behavior;

modification programming means connected to receive said event signals over a first time span during which the habitual behavior naturally occurs and to responsively generate a personalized program for modification of said habitual behavior including a programmed schedule of future occurrence times for actively prompting said events to occur over a second time span; and output means connected to actively signal a human user to engage in another occurrence of said discrete event by outputting a humanly sensible stimulus at said scheduled future occurrence times, which stimulus is capable of interrupting the human user activity to actively stimulate such further occurrence even though the apparatus may be out of the user's sight;

wherein said predetermined pattern of human behavior is a time sequence of cigarette smoking events and wherein said modification programming means monitors the existing pattern of cigarette smoking events over said first time span comprising a first plurality of days and then schedules a graduated reduction in the frequency of scheduled future cigarette smoking events over a subsequent second time span comprising a second plurality of days, the elapsed time between scheduled future events increasing according to a prescribed first withdrawal curve from day-to-day and increasing in accordance with a second withdrawal curve within each day of the second time span.

* * * * *

UNITED STATES PATENT AND TRADEMARK OFFICE
CERTIFICATE OF CORRECTION

PATENT NO. : 4,853,854

DATED : August 1, 1989

INVENTOR(S) : Albert Behar; Orna Behar; Lee W. Frederiksen; Donald A. Howard-Link and Catherine Timmerman It is certified that error appears in the above-identified patent and that said Letters Patent is hereby corrected as shown below:

In the drawings, Sheet 10, Fig. 9, adjacent to the vertical arrow below the parallelogram labeled "CNTON=0 ?" insert --Y--. Column 1, line 12, delete "can be". Column 7, line 20, "LCD remains" should read --LCD and remains--. Column 9, line 58, "smokig" should read --smoking--; line 62, "as last" should read -- was last--. Column 10, line 50, "processor" should read --processor 238--; line 52, "tubular" should read --tabular--. Column 11, line 54, delete the first occurrence of "with". Column 13, line 36, "For exemplary" should read --For the exemplary--. Column 15, line 38, "STIM-1" should read --STIM=1--. Column 18, line 17, "LD" should read --LCD--; line 63, "p=1" should read --p=-1--. Column 19, line 1, "s=1" should read --s=-1--; line 23, "Adaption" should read --Adaptation--. Column 26, line 30, "output times" should read --output means in response to sensing the occurrence of an event signal at times--.

Signed and Sealed this

Twenty-ninth Day of January, 1991

Attest:

HARRY F. MANBECK, JR.

Attesting Officer

Commissioner of Patents and Trademarks